United States Patent
Seeberger et al.

(10) Patent No.: US 6,323,339 B1
(45) Date of Patent: Nov. 27, 2001

(54) SYNTHESIS OF OLIGOSACCHARIDES, REAGENTS AND METHODS RELATED THERETO

(75) Inventors: Peter H. Seeberger, Cambridge; Obadiah J. Plante, Beverly, both of MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/413,381

(22) Filed: Oct. 6, 1999

Related U.S. Application Data

(60) Provisional application No. 60/103,291, filed on Oct. 6, 1998.

(51) Int. Cl.[7] .................................. C07H 1/00; C07F 9/28
(52) U.S. Cl. ..................... 536/124; 536/117; 536/124; 536/18.6; 536/17.9; 536/123.1; 536/123.13; 549/222
(58) Field of Search ................... 536/109, 124, 536/123.1, 123.13, 117, 18.6, 17.9; 549/222

(56) References Cited

U.S. PATENT DOCUMENTS 4,785,084 * 11/1988 Warren et al. .
5,095,123 * 3/1992 Sabesan .

(List continued on next page.)

FOREIGN PATENT DOCUMENTS

| WO 96/24683 | 8/1996 | (WO) . |
| WO 96/32491 | 10/1996 | (WO) . |
| WO 98/46784 | 10/1998 | (WO) . |
| WO 99/28491 | 6/1999 | (WO) . |
| WO 99/47694 | 9/1999 | (WO) . |
| WO 99/47695 | 9/1999 | (WO) . |
| WO 00/20428 | 4/2000 | (WO) . |

OTHER PUBLICATIONS

Hashimoto et al. ""Armed–Disarmed" glycosidation strategy based on glycosyl donors and acceptors carrying phosphoramidate as a leaving group: a convergent synthesis of Globotriaosylceramide". Tetrahedron Letters, vol. 38, No. 52, 8969–8972, 1997.*

Liang et al. "Parallel synthesis and screening of a solid phase carbohydrate library". Science, vol. 274, pp. 1520–1522, 1996.*

Paulsen et al. "Synthese von DD–Heptosephophaten als substrate oder potentielle inhibitoren fur die Heptose–Synthetase". Liebigs Ann. Chem., 1994, pp. 389–397.*

Plante et al. "Anomeric Phosphorodithioates as novel glycosylating agents". J.Org.Chem., vol. 63, 1998, pp. 9150–9151.*

Chen, et al. "Glycosyl Phosphoramidimidates As Versatile Glycosyl Donors", Heterocycles, 45(7): 1247–1250 (1997).

Hashimoto, et al.; ""Armed Diarmed" Glycosidation Strategy Based on Glycosyl Donors and Acceptors Carrying Phosphoroamidate as a Leaving Group: A Convergent Synthesis of Globotriaosylceramide", Tetrahedron Letters 38 (52): 8969–8972 (1997).

(List continued on next page.)

*Primary Examiner*—Gary Geist
*Assistant Examiner*—Devesh Khare
(74) *Attorney, Agent, or Firm*—Dana M. Gordon; Foley, Hoag & Eliot LLP

(57) ABSTRACT

One aspect of the present invention relates to differentially protected glycosyl phosphates. Another aspect of the present invention relates to the preparation of glycosyl phosphates from glycal precursors. In another aspect of the present invention, glycosyl phosphates are used as glycosyl donors in glycosylation reactions.

19 Claims, 9 Drawing Sheets

U.S. PATENT DOCUMENTS

| | | | |
|---|---|---|---|
| 5,369,017 | 11/1994 | Wong et al. | 435/68.1 |
| 5,374,655 | 12/1994 | Kashem et al. | 514/540 |
| 5,516,665 | 5/1996 | Wong | 435/97 |
| 5,716,812 | 2/1998 | Withers et al. | 435/74 |
| 5,721,338 | 2/1998 | Imperiali et al. | 530/317 |
| 5,728,554 | 3/1998 | Bayer et al. | 435/97 |
| 5,759,823 | 6/1998 | Wong et al. | 435/97 |
| 5,811,539 | 9/1998 | Seiffert-Stoeriko et al. | 536/26.8 |
| 5,922,577 | 7/1999 | Defrees et al. | 435/97 |
| 5,952,203 | 9/1999 | Withers et al. | 435/97 |
| 5,952,454 | 9/1999 | Kovac et al. | 528/332 |
| 5,994,502 | 11/1999 | Imperiali et al. | 530/344 |
| 6,013,779 | 1/2000 | Wong et al. | 536/18.6 |
| 6,022,713 | 2/2000 | Noguchi et al. | 435/89 |
| 6,030,815 | 2/2000 | Defrees et al. | 435/97 |
| 6,077,695 | 6/2000 | Nilsson | 435/84 |

OTHER PUBLICATIONS

Hashimoto, et al.; "A Rapid and Efficient Synthesis of 1,3–trans–β–Linked Glycosides via Benzyl–or Benzoyl–Protected Glycopyranosyl Phosphates", J. Chem. Soc. Chem. Commun. pp. 685–687 (1989).

Laupichler, et al.; "Convenient Iodonium–Promoted Stereoselective Synthesis of 2–Deoxy–α–glycosides by Use of S–(2–Deoxyglycosyl) Phosophorodithioates as Donors", Synthesis, pp. 1133–1136 (Nov. 1992).

Liang, et al.; "Parallele Synthesis and Screening of a Solid Phase Carbohydrate Library", Science, 274: 1520–1522 (Nov. 29, 1996).

Paulsen et al.; "Synthese Von DD–Heptosephosphaten als Substrate oder Potentielle Inhibitoren für die Heptose–Synthetase", Liebigs Ann. Chem. pp. 389–397 (1994).

Plante and Seeberger; "Anomeric Phosphorodithioates as Novel Glycosylating Agents", J. Org. Chem. 63: 9150–9151 (1998).

Timmers, et al. "An Expeditious Route to *Streptococci* and *Enterococci Glycolipids* VLA Ring–Opening of 1.2—Anhydrosugars", J. Carbohydrate Chemistry 17 (3): 471–487 (1998).

Watanabe, et al.; "Dibenzyl Phosphorofluoridate, A New Phosphorylating Agent", Tetrahedron Letters 29 (45) pp. 5763–5764 (1988).

International Search Report.

Hashimoto et al.; "Oligosaccharide Synthesis Based on Glycosyl Donors and Acceptors Carrying Phosphorus–Containing Leaving Groups", Tetrahedron Letters 38 (29): 5181–5184 (1997).

Morales et al.; "Carbohydrate—Carbohydrate Interactions in Water with Glycophanes as Model Systems", J. Org. Chem. 63: 9212–9222 (1998).

Plante and Seeberger; "Anomeric Phosphorodithioates as Novel Glycosylating Agents", J. Org. Chem. 63: 9150–9151 (1998).

Seeberger et al., "Synthesis of Biologically Important Oligosaccharides and Other Glycoconjugates by the Glycal Assembly Method", Aldrichimica Acta 30 (3): 75–92 (1997).

Zheng et al., "Solid Support Oligosaccharide Synthesis: Construction of β–Linked Oligosaccharides by Coupling of Glycal Derived Thioethyl Glycosyl Donors", J. Org. Chem. 63:1126–1130 (1998).

* cited by examiner

Table 2. Glycosylations Using Glycosyl Phosphates and Trimethylsilyltriflate.[a]

| Entry | Glycosyl Donor | Glycosyl Acceptor | Product | Yield |
|---|---|---|---|---|
| 1 | 2β | 9 | 13 | 94 |
| 2 | 2β | 10 | 14 | 83 |
| 3 | 5β | 9 | 15 | 82 |
| 4 | 8β | 9 | 16 | 71 |
| 5 | 2β | 11 | 17 | 90 |
| 6[b] | 2α | 9 | 13 | 87 |
| 7[b] | 2α | 10 | 14 | 73 |
| 8[b] | 2α | 11 | 17 | 70 |

[a] Glycosylations were carried out with 1.2 equiv donor, 1.0 equiv acceptor and 1.2 equiv TMSOTf in dichloromethane at -78°C.
[b] Reaction was carried out at -20°C.

Fig. 2

UDP-Glucose

Glucose

Galactose

Lactose

SYNTHESIS OF OLIGOSACCHARIDES, REAGENTS AND METHODS RELATED THERETO

RELATED APPLICATIONS

This application claims the benefit of the filing date of U.S. Provisional Patent Application No. 60/103,291, filed Oct. 6, 1998, the specification of which is hereby incorporated by reference.

BACKGROUND OF THE INVENTION

Nucleic acids, proteins and polysaccharides are tree major classes of biopolymers. While the first two systems are principally linear assemblies, polysaccharides are structurally more complex. This structural and stereochemical diversity results in a rich content of "information" in relatively small molecules. Nature further "leverages" the structural versatility of polysaccharides by their covalent attachment (i.e. "conjugation") to other biomolecules such as isoprenoids, fatty acids, neutral lipids, peptides or proteins.

Oligosaccharides in the form of glycoconjugates mediate a variety of events including inflammation, immunological response, metastasis and fertilization. Cell surface carbohydrates act as biological markers for various tumors and as binding sites for other substances including sub pathogens.

More specifically, an increasing number of physiologically important recognition phenomena involving carbohydrates have been discovered in recent years. Lectins, proteins which contain carbohydrate recognition domains, have been identified. Prominent members of the calcium dependent (C-type) lectin family (Drickamer, K. *Curr. Opin. Struct. Biol.* 1993, 3, 393) are the selectins which play a crucial role in leukocyte recruitment in inflammation. Bevilacqua, M. P.; Nelson, R. M. *J Clin. Invest.* 1993, 91, 379. Members of the C-type lectin superfamily have been described on NK cells and Ly-49, NKR-P1 and NKG2 constitute group V of C-type lectins. While many lectins have been purified and cloned, their ligands have not been identified due to the heterogeneous nature of carbohydrates.

The increasing recognition of the key roles of oligosaccharides and glycoconjugates in fundamental life sustaining processes has stimulated a need for access to usable quantities of these materials. Glycoconjugates are difficult to isolate in homogeneous form from living cells since they exist as microheterogeneous mixtures. The purification of these compounds, even when possible, is at best tedious and is generally achieved in very small yields. Given the travails associated with isolation from natural sources, a major opportunity for chemical synthesis presents itself.

Currently three powerful glycosylating agents are commonly used in the synthesis of oligosaccharides in solution and on the solid support. Trichloroacetimidates have been used for over fifteen years for the synthesis of oligosaccharides in solution and very recently on the solid support. The drawback of these excellent synthons is their lengthy synthesis.

Thioethyl glycosides have also been used successfully for the synthesis of olihgosaccharides in solution and on the solid support. Drawbacks are the use of the toxic stench ethanethiol during the synthesis and the requirement for methyl triflate, a carcinogen, as an activator. These drawbacks make the commercialization of this otherwise very attractive class of glycosylating agents nearly impossible.

Glycosyl sulfoxides involve the use of toxic thiols during their synthesis but otherwise can be activated by non-toxic agents. Both the synthesis of oligosaccharides in solution as well as on the solid support has been accomplished using this approach.

The invention of solid phase peptide synthesis by Merrifield 35 years ago dramatically influenced the strategy for the synthesis of biopolymers. The preparation of structurally defined oligopeptides (Atherton, E.; Sheppard, R. C. *Solid phase peptide synthesis: A practical approach*; IRL Press at Oxford University Press: Oxford, England, 1989, pp 203) and oligonucleotides (Caruthers, M. H. *Science* 1985, 230, 281) has benefited greatly from the feasibility of conducting their assembly on various polymer supports. The advantages of solid matrix based synthesis, in terms of allowing for an excess of reagents to be used and in their facilitation of purification are now well appreciated. It is obvious, that the level of complexity associated with the synthesis of an oligosaccharide on a polymer support dwarfs that associated with the other two classes of repeating biooligomers. First, the need to differentiate similar functionality (hydroxyl or amino) in oligosaccharide construction is much more challenging than is the situation with oligopeptides or oligonucleotides. Furthermore, in these latter two cases, there is no stereoselection associated with construction of the repeating amide or phosphate bonds. To the contrary, each glycosidic bond to be fashioned in a growing oligosaccharide ensemble constitutes a new locus of stereogenicity.

Remarkably, a great deal of progress had been achieved in assembling relatively complex carbohydrate ensembles on a solid support. Advances along these lines have involved the need for considerable simplification and refinement of protecting group strategies and the development of glycosylation methodology which is workably stereoselective and amenable to being conducted with one component anchored to an insoluble matrix.

The development of protocols for the solid support synthesis of oligosaccharides and glycopeptides requires solutions to several problems. Of course, considerable thought must be addressed to the nature of the support material. The availability of methods for attachment of the carbohydrate from either the "reducing" or "non-reducing" end would be advantageous. Also, selection of a linker which is stable during the synthesis, but can be easily cleaved when appropriate, is critical. A protecting group strategy that allows for high flexibility is desirable. Most important is the matter of stereospecific and high yielding coupling reactions.

Combinatorial chemistry has been used in the synthesis of large numbers of structurally distinct molecules in a time and resource efficient manner. Peptide, oligonucleotide, and small molecule libraries have been prepared and screened against receptors or enzymes to identify high-affinity ligands or potent inhibitors. For a review see: Thompson, L. A.; Ellman, J. A. *Chem. Rev.* 1996, 96, 555.

Generation of biologically active oligosaccharide libraries presents several interesting challenges. Each glycosidic bond to be fashioned in a growing oligosaccharide constitutes a new locus of stereogenicity, unlike the joining of nucleosides and peptides. Furthermore, the natural mammalian sugar monomers (FIG. 3) all carry at least three hydroxyl groups which can undergo glycosylation. Extensive branching, sulfation and phosphorylation of oligosaccharides are common in nature.

Two different strategies for the generation of combinatorial oligosaccharide libraries have been reported to date. The first approach followed the "random-glycosylation" strategy which is based on the assumption that all hydroxyls of an glycosyl acceptor react at the same rate. Kanie, O.; Barresi, F.; Ding, Y.; Labbe, J.; Otter, A.; Forsberg, L. S.; Ernst, B.; Hindsgaul, O. *Angew. Chem. Int. Ed. Engl.* 1995, 34, 2720. While "random-glycosylation" requires only a very limited number of monosaccharide building blocks, the analysis of the resulting mixtures poses an almost insurmountable problem. For the "site-specific" glycosylation approach to combinatorial oligosaccharide synthesis, differentially protected monosaccharides are employed. In this manner, only one particular hydroxyl group on the monosaccharide may be exposed and coupled. Either, each member of the library is synthesized in a separate reaction vessel (spatially separate synthesis method) or pooling strategies are employed to generate large libraries of compounds (split synthesis method). Very recently a libraxy of approximately 1500 modified oligosaccharides was prepared by the split synthesis method. Liang, R.; Yau, L.; Loebach, J.; Ge, M.; Uozumi, Y.; Sekanina, K.; Horan, N.; Gildersleeve, J.; Thompson, C.; Smith, A.; Biswas, K.; Still, W. C.; Kahne, D. *Science* 1996, 274, 1520. The library was screened for ligands of a lectin, while the compounds were still attached to the solid support. A tagging system was used to rapidly determine the structure of the selected compounds.

The ability to generate diverse combinatorial libraries containing carbohydrates is directly linked to the ability to prepare complex carbohydrates and therefore to the availability of potent glycosylation reactions. Currently three powerful glycosylating agents are commonly used in the synthesis of oligosaccharides in solution and on the solid support. Trichloroacetimidates have been used for over fifteen years for the synthesis of oligosaccharides in solution and very recently on the solid support. The drawback of these excellent synthons is their lengthy synthesis.

Thioethyl glycosides have also been used successfully for the synthesis of oligosaccharides in solution and on the solid support. Drawbacks are the use of the toxic stench ethanethiol during the synthesis and the requirement for methyl triflate, a carcinogen, as an activator. These drawbacks make the commercialization of this otherwise very attractive class of glycosylating agents nearly impossible.

Glycosyl sulfoxides involve the use of toxic thiols during their synthesis but otherwise can be activated by non-toxic agents. Both the synthesis of oligosaccharides in solution as well as on the solid support has been accomplished using this approach.

Thioethyl glycosides and sulfoxides have been used in the synthesis of oligosaccharide libraries. In both cases relatively small diaccharide (~1,500 compounds) and trisaccharide (~50 compounds) libraries were generated. Wong, C.-H.; Ye, X.-S.; Zhang, Z. *J. Am. Chem. Soc.* 1998, 120, 7137. The effort to synthesize the building blocks restricts the amount and the variety of starting materials that can be produced. The possibility to fashion monosacchaide building blocks in an efficient and straightforward fashion from glycal precursors presents a dramatic advantage over existing methods.

The random-glycosylation method by Hindsgaul et al. does not require differentially protected building blocks but does produce mixtures which make screening and identification of library composition impossible. This method is expected to have very limited practical use.

Several challenges have to be met to prepare combinatorial carbohydrate libraries. Synthetic strategies in which either the glycosyl donor or the glycosyl acceptor is attached to the solid support will be employed. A wide variety of differentially protected monosaccharide building blocks have to be prepared. Efficient glycosylation reactions have to be employed. The resulting libraries can be screened for lectin binding while still on the solid support or after already being cleaved.

The generation of combinatorial carbohydrate libraries will facilitate the rapid identification of ligands to many carbohydrate binding proteins which are involved in a variety of important biological events including inflammation (Giannis, A. *Angew. Chem. Int. Ed. Engl.* 1994, 33, 178), immune response (Ryan, C. A. *Proc. Natl. Acad. Sci. U.S.A.* 1994, 91, 1) and metastasis (Feizi, T. *Curr. Opin. Struct. Biol.* 1993, 3, 701). Analogs of ligands can help to define important lectin-ligand interactions. Non-natural ligands can be powerful inhibitors of carbohydrate-protein binding and will facilitate the study of cascade-like events involving such interactions. Furthermore, inhibitors of carbohydrate-lectin binding are potential candidates for a variety of therapeutic applications.

SUMMARY OF THE INVENTION

Glycosyl phosphates are described; these compounds are novel, extremely powerful glycosyl donors. The glycosyl phosphates were synthesized in a highly efficient one-pot, two step synthesis from differentially protected glycal precursors which are commercially available. Coupling protocols employing a non-toxic activator were used to fashion glycosidic linkages selectively and in high yield with a variety of glycosyl acceptors. Orthogonal glycosylation schemes employing glycosyl phosphates and thioethyl glycosides have been developed for the rapid assembly of oligosaccharide structures. The glycosylation protocols are applicable to the synthesis of complex oligosaccharides on a solid support. A detailed strategy is described for the use of glycosyl phosphates in a coupling cycle that will ultimately be amenable to automation.

Also described is a novel approach to the chemical synthesis of combinatorial carbohydrate libraries on a solid support. Synthetic strategies in which either the glycosyl donor or the glycosyl acceptor is attached to the solid support will be employed. Glycosyl phosphates which can be accessed rapidly from differentially protected glycal precursors serve as building blocks for the oligosaccharide libraries. A diverse pool of oligosaccharides and non-natural analogs including sulfated and phosphorylated carbohydrates can be generated using the outlined methodology. The resulting libraries can be screened for high-affinity ligands of carbohydrate binding proteins (lectins) involved in a host of biological functions including inflammation, immune response and cancer. Inhibitors of carbohydrate-lectin binding are potential candidates for a variety of therapeutic applications.

The chemistry outlined herein is expected to allow for the automated synthesis of oligosaccharides and glycoconjugates much in the same fashion that peptides and oligonucleotides are currently assembled. The ability to synthesize defined biologically important glycoconjugates are far reaching with many direct applications to biomedical questions. Opportunities for the application of the present invention include the production of synthesis building blocks, biotechnology applications and the development of automated oligosaccharide synthesis machines.

BRIEF DESCRIPTION OF THE FIGURES

FIG. 2 depicts the results of certain glycosylation reactions using glycosyl phosphates activated with trimethylsilyl triflate.

DETAILED DESCRIPTION OF THE INVENTION

Glycosyl Phosphate-Based Synthesis of Oligosaccharides in Solution and on Solid Support A wide range of increasingly powerful chemical glycosylation methods has been developed to meet the demand for synthetic oligosaccharides and glycopeptides. A variety of different glycosyl donors including anomeric trichloroacetimidates (Schmidt, R. R. *Angew. Chem. Int. Ed. Engl.* 1986, 25, 212), N-pentenylglycosides (Fraser-Reid, B.; Konradsson, P.; Mootoo, D. R.; Udodong, U. *J Chem. Soc. Chem. Comm.* 1988, 823), anomeric fluorides (Mukaiyama, T.; Murai, Y.; Shoda, S. *Chem. Lett.* 1981, 431), anomeric aryl sulfoxides (Kahne, D.; Yang, D.; Lim, J. J.; Miller, R.; Paguaga, E. *J. Am. Chem. Soc.* 1988, 110, 8716), and thioglycosyl donors (For a review, see: Garegg, P. J. *Adv. Carb. Chem. Biochem.* 1997, 52, 179) have been employed in glycosylation reactions. While much progress has been made, the need for development of powerful new glycosyl donors still remains. Ideally, new glycosyl donors are readily prepared from differentially protected monosaccharide precursors, may be activated to furnish a variety of glycosidic linkages selectively and in high yield, while minimizing the formation of side products under conditions that can be applied in solution and on a solid support.

Figure 1:
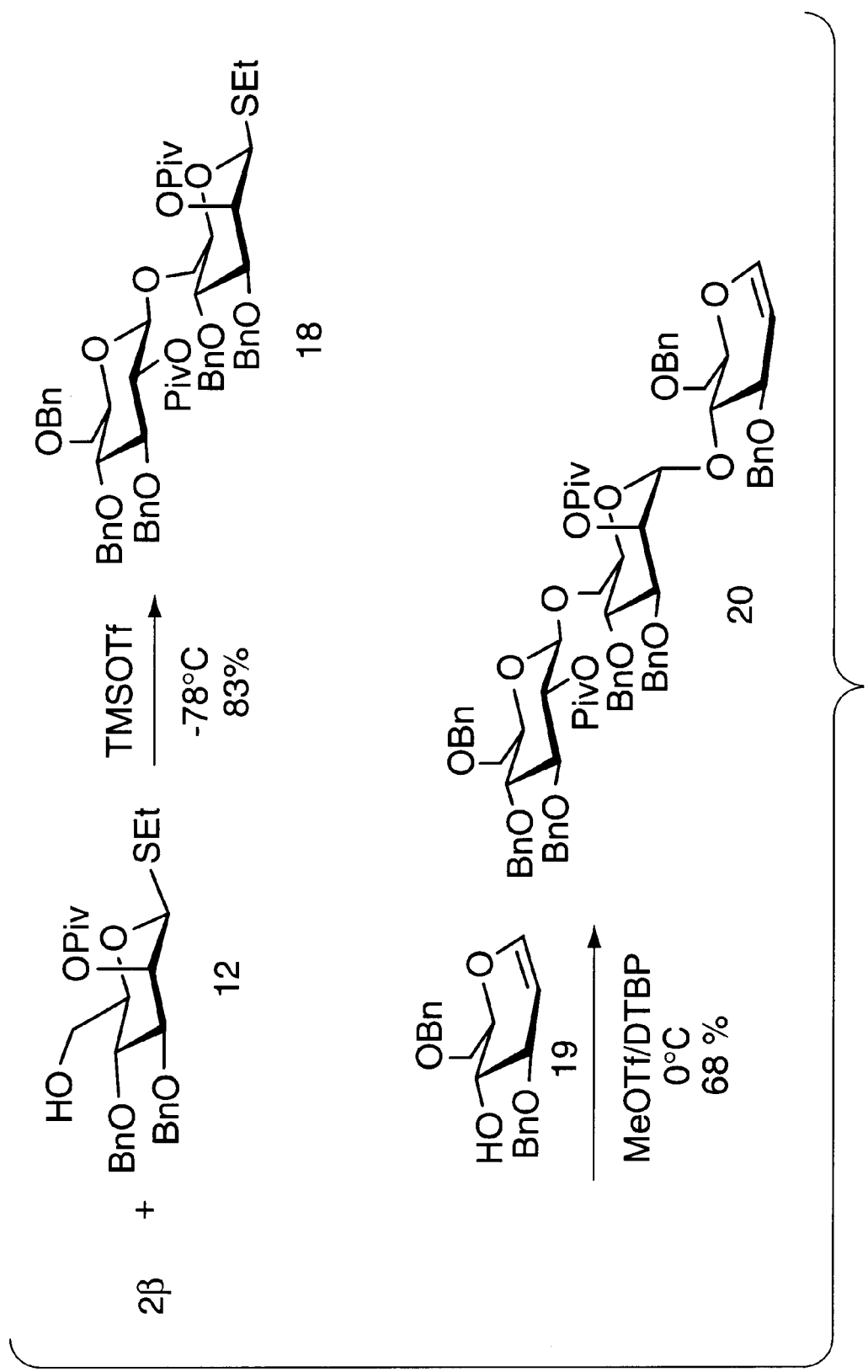
FIG. 1 depicts an example of the orthogonal glycosylation strategy for the synthesis of oligosaccharides, using glycosyl phosphates and thioethyl glycosides.
Figure 3:
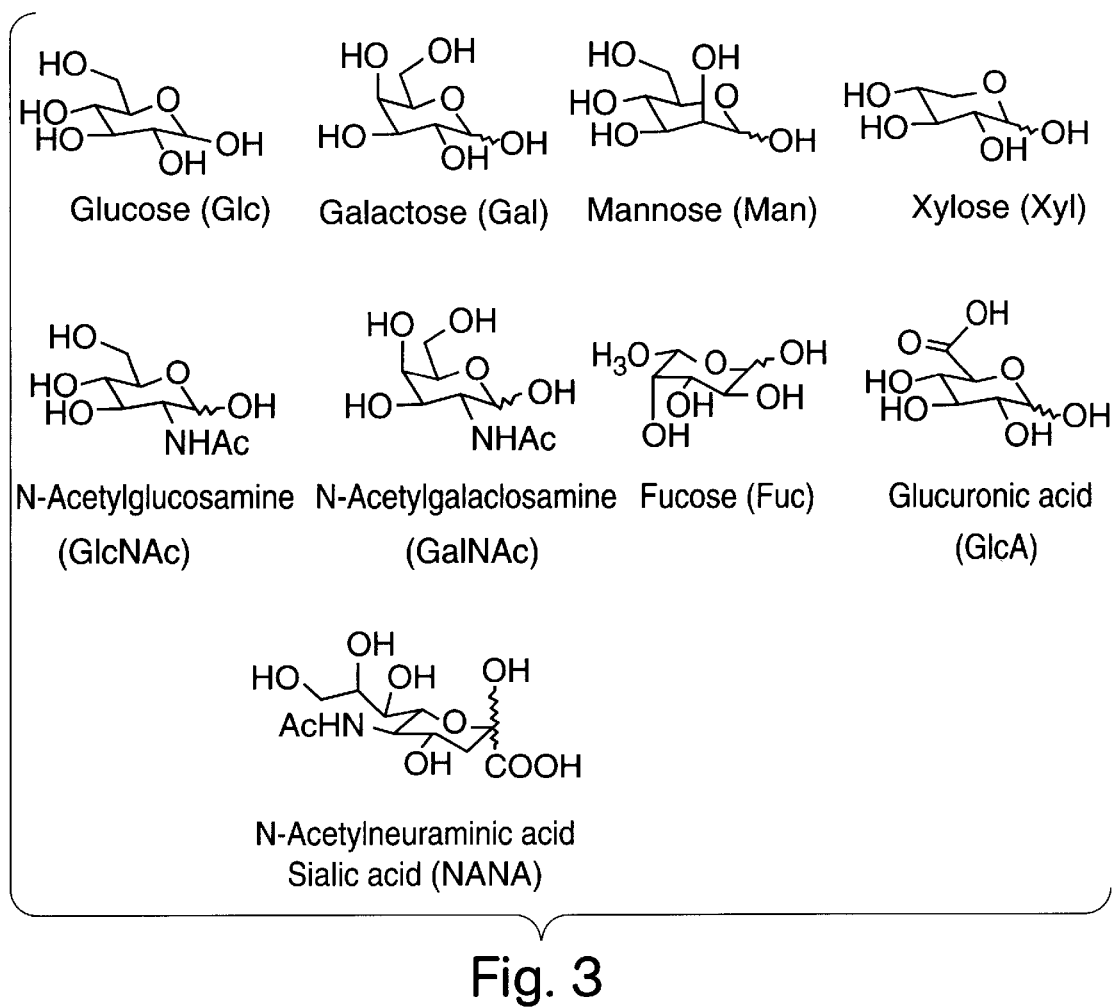
FIG. 3 depicts the most common monosaccharides used in mammalian biosynthesis of glycoconjugates.
Figure 4:
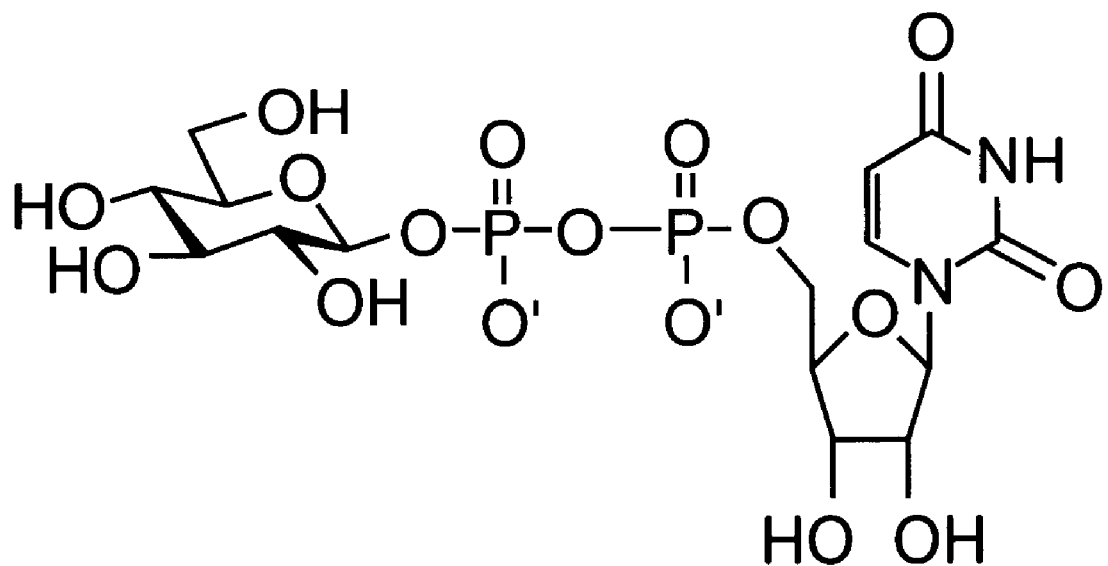
FIG. 4 depicts a sugar nucleotide used in enzymatic glycosylations.
Figure 5:
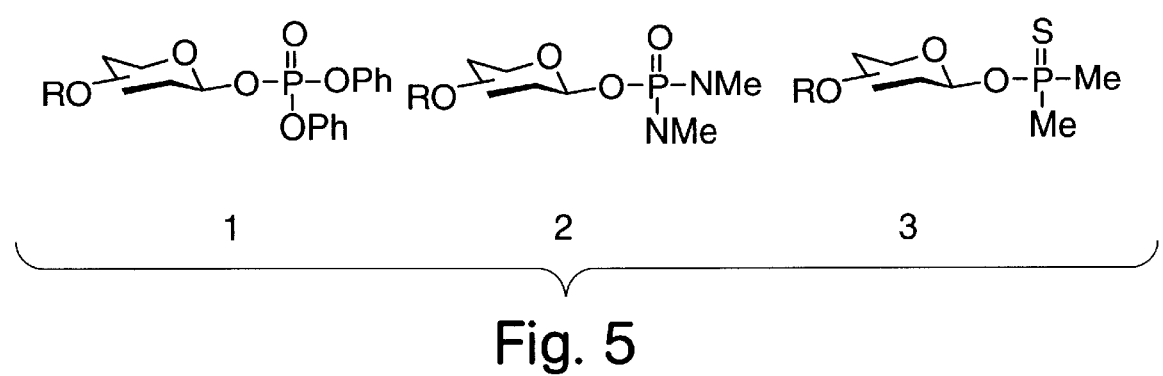
FIG. 5 depicts certain glycosyl phosphates used in glycosylation reactions.

Glycosyl phosphates in form of sugar-nucleosides are of great significance in enzymatic glycosyl transfer reactions (FIG. 4). While many anomeric groups have been evaluated for their use as glycosyl donors (vide supra), anomeric phosphate derivatives have received surprisingly little attention for this purpose. Glycosyl phosphites have proven useful in the synthesis of sialic acid glycosidic linkages (Sim, M. M.; Kondo, H.; Wong, C.-H. *J Am. Chem. Soc.* 1993, 115, 2260) and only few other phosphate derivatives including glycosyl diphenyl phosphates 1 (Hashimoto, S.; Honda, T.; Ikegami, S. *J Chem. Soc. Chem. Commun.* 1989, 685), glycosyl phosphoroamidates 2 (Hashimoto, S.; Yanagia, Y.; Honda, T.; Harada, H.; Ikegami, S. *Tetrahedron Lett.* 1992, 33, 3523), and dimethyl phosphonothioates 3 (Inazu, T.; Hosokawa, H.; Satoh, Y. *Chem. Lett.* 1985, 297), have been described to date (see FIG. 5).

To date, all protocols for the synthesis of anomeric phosphate-based glycosyl donors have relied on the phosphitylation or phosphorylation of an anomeric hydroxyl group following protection and deprotection protocols. The preparation of differentially protected monosaccharide glycosyl donors requires lengthy procedures in many cases. Glycals on the other hand allow for the facile differential protection of the hydroxyl functionalities and have been shown to be versatile starting materials for the synthesis of oligosaccharides and natural products. Seeberger, P. H.; Bilodeau, M. T.; Danishefsky, S. J. *Aldrichimica Acta* 1997, 30, 75.

Conversion of glycals to anomeric phosphates was achieved by epoxidation of the double bond of glycal 4 with dimethyldioxirane (DMDO) to furnish the 1,2-anhydrosugar (Scheme 1). Opening of the epoxide with a phosphoric acid derivative furnished anomeric phosphates which were C-2 protected in situ. Addition of an excess of acetyl chloride, benzoyl chloride or pivaloyl chloride and DMAP followed by purification by filtration through a short pad of silica furnished the desired protected glycosyl phosphates in very good yield (80–85%). The formation of either α or β glycosyl phosphates was achieved by use of THF (almost exclusively α), toluene (almost exclusively β), or dichloromethane (mixture of α and β).

Scheme 1
Synthesis of glycosyl phosphates from glycal precursors

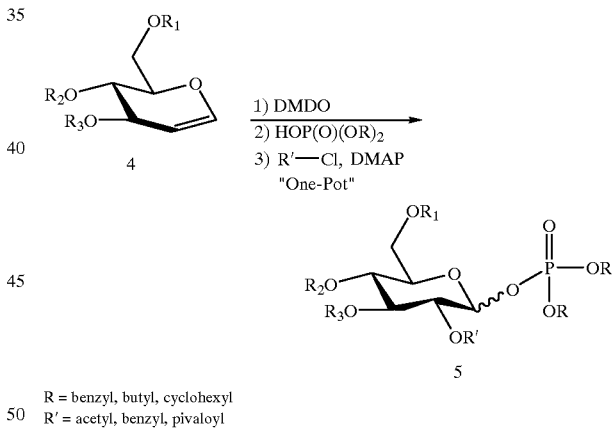

R = benzyl, butyl, cyclohexyl
R' = acetyl, benzyl, pivaloyl

After establishing a short and general synthetic protocol for the preparation of anomeric phosphate derivatives, glycosylation procedures involving these donors have been developed. Following earlier reports on the use of glycosyl phosphates as glycosyl donors, trimethylsilyl triflate (TMSOTf) was employed as a powerful, non-toxic promoter for the glycosylation reactions.

Reaction of the glycosyl phosphates with a variety of acceptors proceeded smoothly (Scheme 2). Different alcohols and thiols were glycosylated in high yields. Solid support-bound nucleophiles could also be used thereby facilitating attachment of a carbohydrate to a solid support matrix.

Scheme 2
Coupling of glycosyl phosphates to a variety of different acceptors.

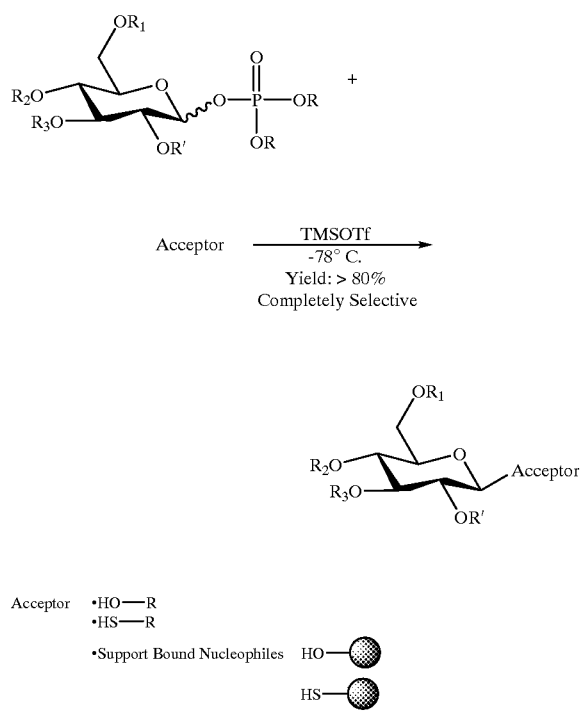

In order to minimize protecting group manipulations during the synthesis of oligosaccharides, different glycosyl donors which may be activated independently by different promoters can be used. This strategy had been developed for the orthogonal use of glycosyl fluorides and thioethyl glycoside glycosyl donors. Described below is the use of glycosyl phosphates in combination with thioethyl glycosides on the example of the synthesis of a trisaccharide.

Scheme 3
Orthogonal synthesis of a trisaccharide using glycosyl phosphates and thioethyl glycosides.

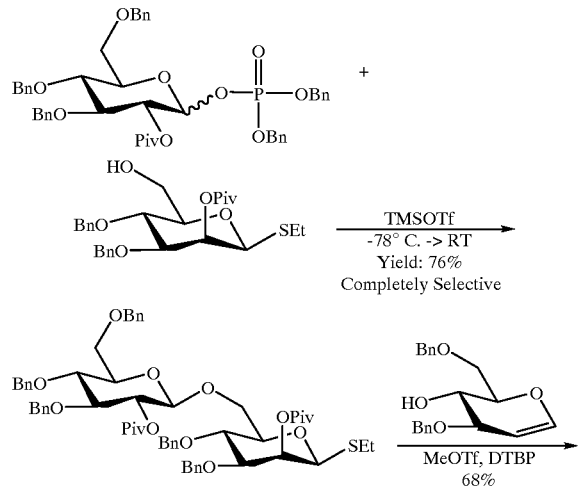

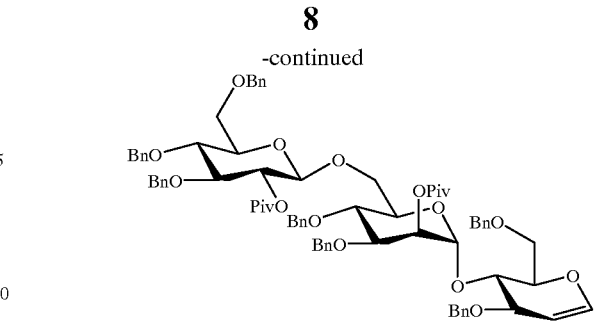

Following the initial studies in a solution phase paradigm, the innovative approaches for the synthesis of glycosidic linkages will be applied to the solid support synthesis of complex oligosaccharides. Both strategies in which the glycosyl donor or the glycosyl acceptor is attached to the solid support will be explored.

In considering how matrix supported synthesis can be applied to the oligosaccharide and broader glycoconjugate problems, two broad strategies present themselves. In one variation, the first carbohydrate is anchored to the support via its "reducing" end (see Scheme I, Case I). The solid support bound carbohydrate will function as an acceptor in the coupling event to a solution-based donor D. As the next cycle is contemplated, a unique acceptor hydroxyl must be exposed in the now elongated, resin bound carbohydrate construct. This strategy demands that in Case I, the donor (D) employed in the previous glycosidation step would have been finished with a uniquely removable blocking group at the site of the next proposed elongation.

Alternatively, the oligomer undergoing elongation may be mounted to the support somewhere in a "non-reducing" region, with the reducing and glycosyl donating available for coupling with solution based acceptor A (Case II). The use of A, of course, demands that the precise acceptor site be properly identified. Furthermore, (and, as was the situation in Case I) in anticipation of the next coupling event, the reducing end of acceptor A (Case II acceptor) is so functionalized, that a new donor capability can be installed at the anomeric carbon of the elongated construct, Both general schemes for the synthesis of oligogaccharides on the solid support are currently being explored for the preparation of oligosaccharides employing glycosyl phosphates.

Scheme 4
Glycosyl acceptor (case 1) and donor (case 2) bound to the solid support. S, solid support; P, unique protecting group; X, activating group; *, uniquely differentiated hydroxyl group Case 1

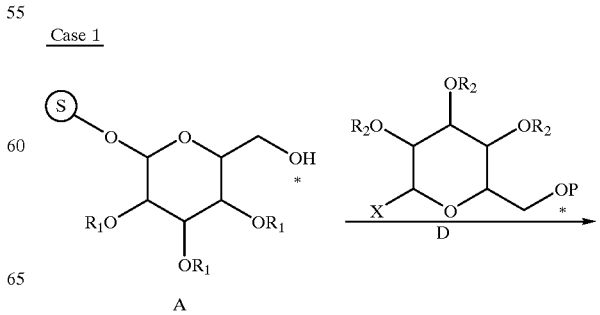

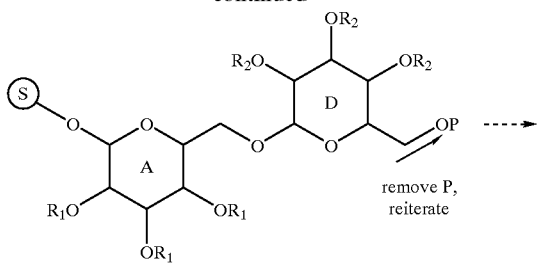

Case 2

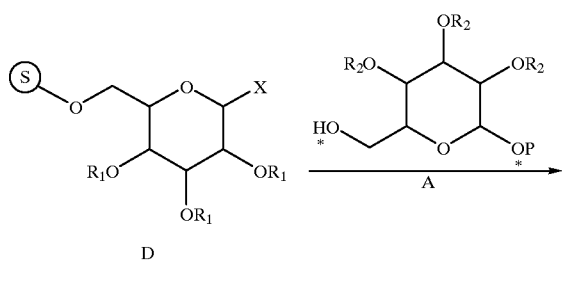

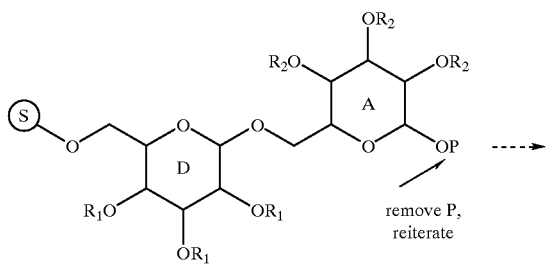

The choice of the solid support is of importance with regard to several aspects of the synthesis. Polystyrene supports crosslinked with 1% divinylbenzene have successfully been used in the preparation of peptides. Low cost, high loading capacity, and stability to a wide variety of reagents are advantages of this polymer. Disadvantage is the limited range of solvents (DMF, $CH_2Cl_2$) which allows for sufficient swelling of this resin.

Novel copolymers of polystyrene and polyethylene glycol (PEG) have been developed to guarantee swelling of these supports in solvents ranging from water to toluene, thus allowing for the possibility to perform screening experiments of molecules still attached to the bead. Drawbacks of these polymers are lower loading and high price.

Controlled pore glass (CPG) has been used for the synthesis of oligonucleotides on the solid support. This non-swelling support may be used in a range of different solvents but has only very limited loading capacities.

Currently all three of these supports are under evaluation for their use in oligosaccharide synthesis using glycosyl phosphates.

The connection of the first monosaccharide to the solid support is accomplished through a linker which can be viewed as a support-bound protecting group. A variety of linkers have previously been prepared for the attachment of hydroxyl and amino groups to the solid phase. Our studies into solid support oligosaccharide synthesis will make use of some of these earlier advances.

The anomeric hydroxyl group is attached through either a linker that leaves a hydroxyl group after cleavage from the solid support or through a spacer element which is connected through the anomeric position as an alcohol. This spacer element ends in a carboxylic acid moiety which may be connected to the solid support through linkers commonly used in peptide synthesis.

Scheme 5
Linkers used in the solid support synthesis of oligosaccharides.

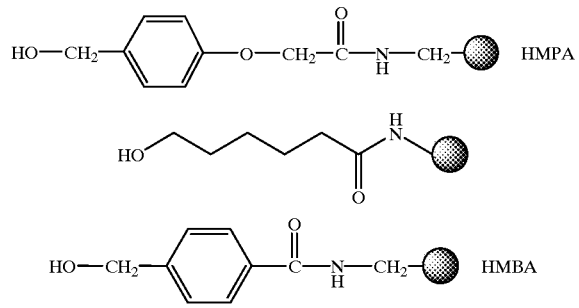

The linkers described here are stable to the coupling and deprotection conditions outlined below and can be cleaved at the end of the synthesis.

Couplings on the solid support are carried out in the same fashion as described for the solution phase couplings. Typically 3–4 equivalents of the glycosyl phosphate donor in solution is added to the solid support containing an immobilized acceptor. Coupling is carried out at –40° C. by addition of trimethyl silyl triflate and coupling times of 30 minutes.

The synthesis oligosaccharides on the solid support requires the development of a coupling cycle which consists of a series of operations required to elongate the growing chain by one unit. The coupling cycle envisioned for the application of glycosyl phosphates on the solid support is outlined in Scheme 6. Attachment of an appropriately protected monosaccharide through its reducing end is followed by removal of a protecting group from a uniquely designated hydroxyl group. Silyl ethers will be used as temporary protecting groups to be cleaved during deprotection using HF-pyridine. Washing steps to clean the resin follow. The exposed hydroxyl group functions as a glycosyl acceptor during the coupling step by reaction with the glycosyl phosphate glycosyl donor (3–4 equivalents) in the presence of TMS triflate as an activator. After several washing steps any unreacted glycosyl acceptor hydroxyl groups are capped off by reaction with acetic anhydride to prevent the formation of deletion sequences by reaction of these sites during subsequent coupling cycles. Repetition of this cycle will lead to the formation of oligosaccharides containing β-glycosidic linkages. Cleavage from the solid support and final deprotection followed by purification are expected to yield the desired oligosaccharide product.

Scheme 6
Solid support synthesis of oligosaccharides using glycosyl phosphates as glycosylating agents.

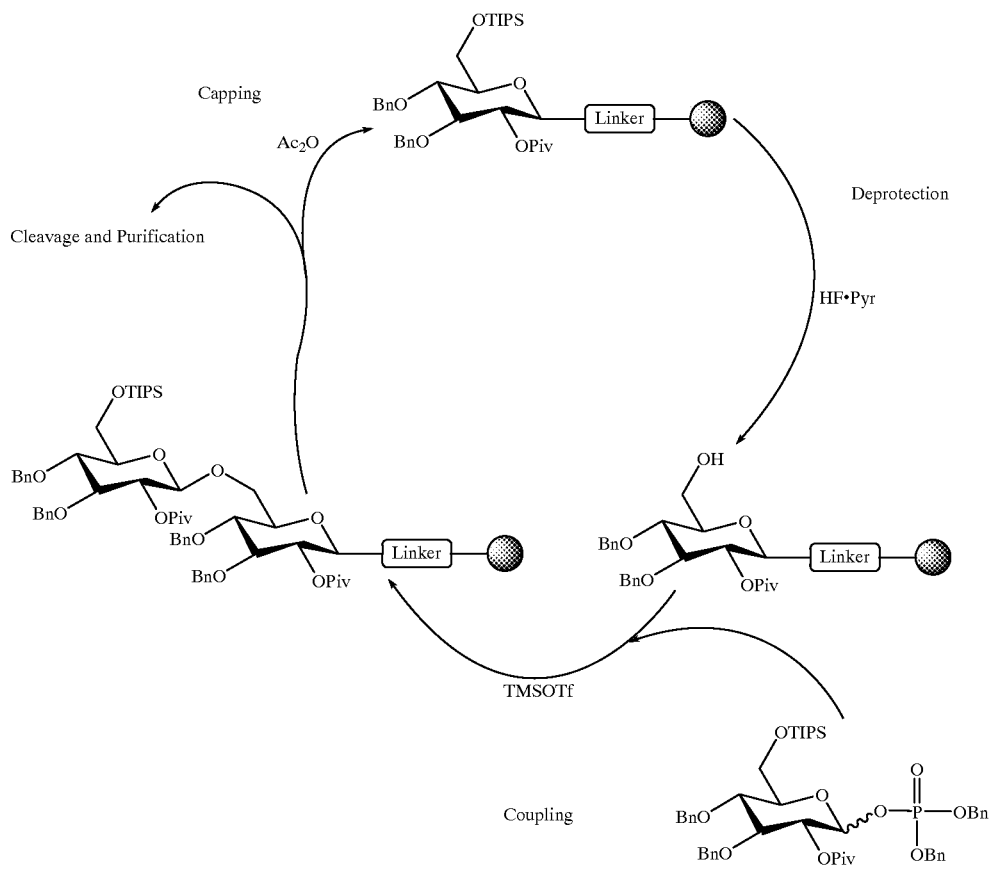

The coupling cycle outlined above consists of a series of relatively simple steps which lend themselves for automation. An automated oligosaccharide synthesizer based on the coupling cycle would have to provide the capability to cool the reaction chamber to −40° C. during the coupling step. All other operations would be similar to operations carried out on automated oligonucleotide or oligopeptide synthesizers.

Glycosyl phosphates combine the advantages of several of the established glycosylation methods while avoiding most of their disadvantages. The differentially protected glycal precursors require only minimal protecting group manipulations and can be converted into glycosyl phosphates in a high yielding, straightforward one-pot procedure. Activation of the glycosyl phosphates occurs at very low temperatures using non-toxic activators and resulting in very high yields and complete selectivity.

The technology outlined here holds the potential to advance the field of glycobiology much like the invention of the DNA synthesizer impacted the field of biotechnology. A host of biomedical applications exists for synthetic oligosaccharides. Not only single compounds but combinatorial carbohydrate libraries could be generated using the technology outlined above. The generation of combinatorial carbohydrate libraries and their application is discussed below.

Certain Compounds of the Invention

In certain embodiments, the compounds of the present invention are represented by generalized structure 1:

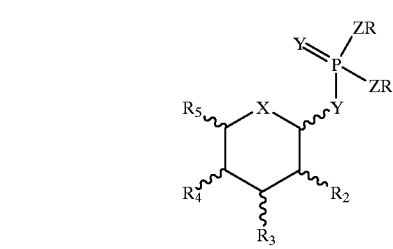

wherein
  X represents O, NR', or S;
  Y represents independently for each occurrence O, NR', or S;
  Z represents independently for each occurrence O, NR', or S;
  R is selected, independently for each occurrence, from the group consisting of H, alkyl heteroalkyl, aryl, arlkl, heteroaryl, and heteroaralkyl;
  R' is selected, independently for each occurrence, from the group consisting of H, alkyl, heteroalkyl, aryl, aralkyl, heteroaryl, heteroaralkyl, acyl, and sulfonyl;
  $R_2$, $R_3$, and $R_4$ are independently selected from the group consisting of R, —OR', —SR', —NR'$_2$, —OSO$_3$H, —OPO$_3$H$_2$;

$R_5$ is selected from the group consisting of R, —$(CR_2)_n$OR', —$(CR_2)$SR', and —$(CR_2)_n$NR'$_2$; and n is an integer selected from the range 0 to 10 inclusive.

In certain embodiments, the compounds of the present invention are represented by 1 and the attendant definitions, wherein X represents O or NR'.

In certain embodiments, the compounds of the present invention are represented by 1 and the attendant definitions, wherein X represents O.

In certain embodiments, the compounds of the present invention are represented by 1 and the attendant definitions, wherein Y represents O.

In certain embodiments, the compounds of the present invention are represented by 1 and the attendant definitions, wherein Y represents S.

In certain embodiments, the compounds of the present invention are represented by 1 and the attendant definitions, wherein Z represents O.

In certain embodiments, the compounds of the present invention are represented by 1 and the attendant definitions, wherein Z represents S.

In certain embodiments, the compounds of the present invention are represented by 1 and the attendant definitions, wherein X represents O or NR'; and Y represents O.

In certain embodiments, the compounds of the present invention are represented by 1 and the attendant definitions, wherein X represents O or NR'; and Y represents S.

In certain embodiments, the compounds of the present invention are represented by 1 and the attendant definitions, wherein X represents O or NR'; and Z represents O.

In certain embodiments, the compounds of the present invention are represented by 1 and the attendant definitions, wherein X represents O or NR'; and Z represents S.

In certain embodiments, the compounds of the present invention are represented by 1 and the attendant definitions, wherein X represents O; and Y represents O.

In certain embodiments, the compounds of the present invention are represented by 1 and the attendant definitions, wherein X represents O; and Y represents S.

In certain embodiments, the compounds of the present invention are represented by 1 and the attendant definitions, wherein X represents O; and Z represents O.

In certain embodiments, the compounds of the present invention are represented by 1 and the attendant definitions, wherein X represents O; and Z represents S.

In certain embodiments, the compounds of the present invention are represented by 1 and the attendant definitions, wherein X represents O; Y represents O or S; and Z represents O or S.

In certain embodiments, the compounds of the present invention are represented by 1 and the attendant definitions, wherein X represents O; Y represents O; and Z represents O or S.

In certain embodiments, the compounds of the present invention are represented by 1 and the attendant definitions, wherein X represents O; Y represents S; and Z represents O or S.

In certain embodiments, the compounds of the present invention are represented by 1 and the attendant definitions, wherein X represents O; Y represents O; and Z represents O.

In certain embodiments, the compounds of the present invention are represented by 1 and the attendant definitions, wherein X represents O; Y represents O; and Z represents S.

In certain embodiments, the compounds of the present invention are represented by 1 and the attendant definitions, wherein X represents O; Y represents S; and Z represents O.

In certain embodiments, the compounds of the present invention are represented by 1 and the attendant definitions, wherein X represents O; Y represents S; and Z represents S.

In certain embodiments, the compounds of the present invention are represented by 1 and the attendant definitions, wherein said compound is represented by one of the following structures:

Glucose

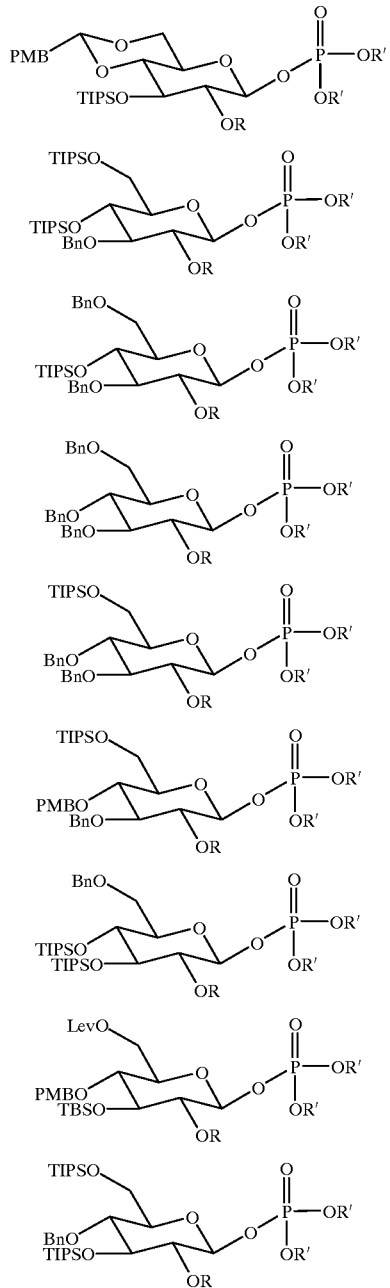

Galactose

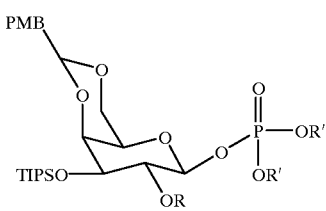

-continued

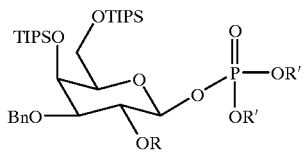

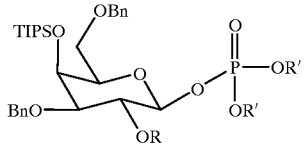

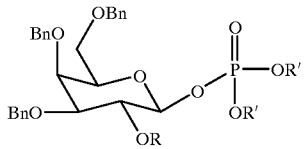

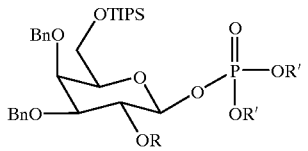

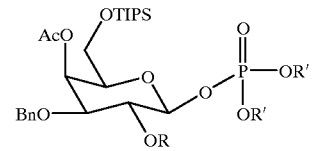

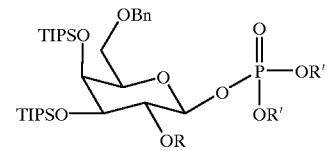

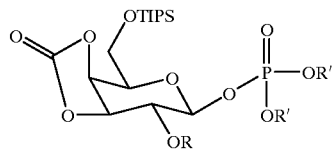

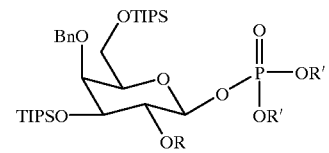

Lactose

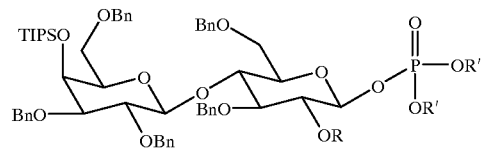

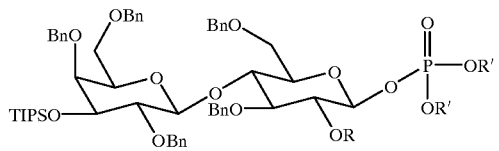

-continued

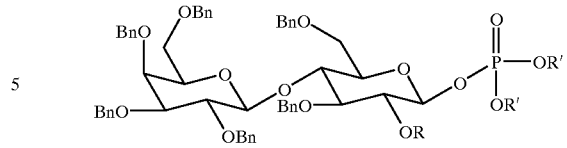

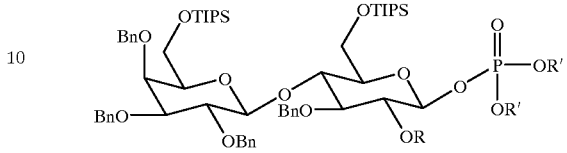

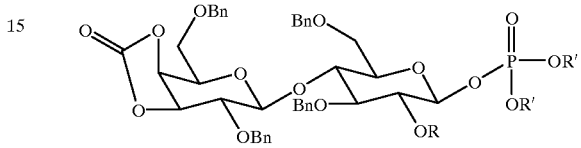

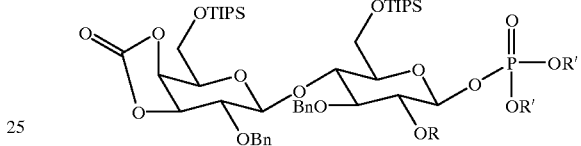

In certain embodiments, the compounds of the present invention are represented by 1 and the attendant definitions, wherein the compound is not 38, 39, or 40.

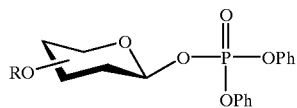
38

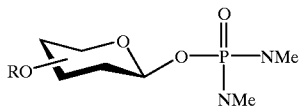
39

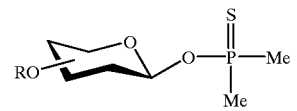
40

Certain Methods of the Invention

In certain embodiments, the present invention relates to a method of preparing compounds represented by 1 and the attendant definitions, wherein said method is represented by the following scheme:

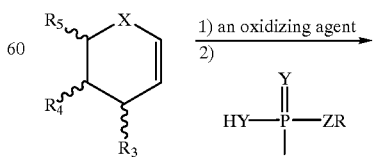

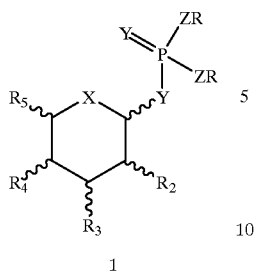

1 wherein
X represents O, NR', or S;
Y represents independently for each occurrence O, NR', or S;
Z represents independently for each occurrence O, NR', or S;
the oxidizing agent is selected from the group consisting or dioxiranes, percarboxylates, and persulfates;
R is selected, independently for each occurrence, from the group consisting of H, alkyl, heteroalkyl, aryl, aralkyl, heteroaryl, and heteroaralkyl;
R' is selected, independently for each occurrence, from the group consisting of H, alkyl, heteroalkyl, aryl, aralkyl, heteroayl, heteroarikyl, acyl and sulfonyl;
$R_2$ is OR';
$R_3$, and $R_4$ are independently selected from the group consisting of R, —OR', —SR', —NR'$_2$, —OSO$_3$H, —OPO$_3$H$_2$;
$R_5$ is selected from the group consisting of R, —(CR$_2$)$_n$OR', —(CR$_2$)$_n$SR', and —(CR$_2$)$_n$NR'$_2$; and
n is an integer selected from the range 0 to 10 inclusive.

In certain embodiments, the present invention relates to the preceding method and the attendant definitions, wherein the oxidizing agent is a dioxirane.

In certain embodiments, the present invention relates to the preceding method and the attendant definitions, wherein the oxidizing agent is dimethyl dioxirane (DMDO).

In certain embodiments, the present invention relates to a method of glycosylating a substrate, comprising the step of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate.

In certain embodiments, the present invention relates to a method of glycosylating a substrate, comprising the steps of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate; and
purifying said glycosylated substrate.

In certain embodiments, the present invention relates to a method of glycosylating a substrate, comprising the step of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate; and
combining said glycosylated substrate with a compound represented by 1 and the attendant definitions under reaction conditions whereby an —OH, —NH—, or —SH moiety of said glycosylated substrate reacts with said compound represented by 1 and the attendant definitions to produce a glycosylated substrate comprising at least two sugar moieties derived form compounds represented by 1 and the attendant definitions.

In certain embodiments, the present invention relates to a method of glycosylating a substrate, comprising the steps of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate;
purifying said glycosylated substrate; and
combining said glycosylated substrate with a compound represented by 1 and the attendant definitions under reaction conditions whereby an —OH, —NH—, or —SH moiety of said glycosylated substrate reacts with said compound represented by 1 and the attendant definitions to produce a glycosylated substrate comprising at least two sugar moieties derived from compounds represented by 1 and the attendant definitions.

In certain embodiments, the present invention relates to a method of glycosylating a substrate, comprising the step of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate, wherein said reaction conditions comprise a Lewis acid.

In certain embodiments, the present invention relates to a method of glycosylating a substrate, comprising the steps of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate, wherein said reaction conditions comprise a Lewis acid; and
purifying said glycosylated substrate.

In certain embodiments, the present invention relates to a method of glycosylating a substrate, comprising the step of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate, wherein said reaction conditions comprise a Lewis acid; and
combining said glycosylated substrate with a compound represented by 1 and the attendant definitions under reaction conditions whereby an —OH, —NH—, or —SH moiety of said glycosylated substrate reacts with said compound represented by 1 and the attendant definitions to produce a glycosylated substrate comprising at least two sugar moieties derived from compounds represented by 1 and the attendant definitions, wherein said reaction conditions comprise a Lewis acid.

In certain embodiments, the present invention relates to a method of glycosylating a substrate, comprising the step of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate, wherein said reaction conditions comprise a silyl sulfonate.

In certain embodiments, the present invention relates to a method of glycosylating a substrate, comprising the steps of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate, wherein said reaction conditions comprise a silyl sulfonate; and
purifying said glycosylated substrate.

In certain embodiments, the present invention relates to a method of glycosylating a substrate, comprising the step of
combining a compound represented by 1 and the attendant definitions with a substrate comprising an —OH, —NH—, or —SH moiety under reaction conditions whereby said moiety of said substrate reacts With said compound represented by 1 and the attendant definitions to produce a glycosylated substrate, wherein said reaction conditions comprise a silyl sulfonate; and
combining said glycosylated substrate with a compound represented by 1 and the attendant definitions under reaction conditions whereby an —OH, —NH—, or —SH moiety of said glycosylated substrate reacts with said compound represented by 1 and the attendant definitions to produce a glycosylatod substrate comprising at least two sugar moieties derived from compounds represented by 1 and the attendant definitions, wherein said reaction conditions comprise a silyl sulfonate.

In certain embodiments, the present invention relates to a method of glycosylating a substrate, comprising the step of:
combining a compound represented by 1 and the attendant definitions with a substrate comprising an —OH, —NH, or —SH moiety under reaction conditions whereby said moiety of said substrate reacts with said compound represented by 1 and the attendant definitions to produce a glycosylated substrate, wherein said reaction conditions comprise a silyl triflate.

In certain embodiments, the present invention relates to a method of glycosylating a substrate, comprising the steps of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate, wherein said reaction conditions comprise a silyl triflate; and
purifying said glycosylated substrate.

In certain embodiments, the present invention relates to a method of glycosylating a substrate, comprising the step of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate, wherein said reaction conditions comprise a silyl triflate; and
combining said glycosylated substrate with a compound represented by 1 and the attendant definitions under reaction conditions whereby an —OH, —NH—, or —SH moiety of said glycosylated substrate reacts with said compound represented by 1 and the attendant definitions to produce a glycosylated substrate comprising at least two sugar moieties derived from compounds represented by 1 and the attendant definitions, wherein said reaction conditions comprise a silyl triflate.

In certain embodiments, the present invention relates to a method of glycosylating a substrate, comprising the step of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate, wherein said reaction conditions comprise a trialkylsilyl triflate.

In certain embodiments, the present invention relates to a method of glycosylating a substrate, comprising the steps of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate, wherein said reaction conditions comprise a trialkylsilyl triflate; and
purifying said glycosylated substrate.

In certain embodiments, the present invention relates to a method of glycosylating a substrate, comprising the step of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate, wherein said reaction conditions comprise a trialkylsilyl triflate; and
combining said glycosylated substrate with a compound represented by 1 and the attendant definitions under reaction conditions whereby an —OH, —NH—, or —SH moiety of said glycosylated substrate reacts with said compound represented by 1 and the attendant definitions to produce a glycosylated substrate comprising at least two sugar moieties derived from compounds represented by 1 and the attendant definitions, wherein said reaction conditions comprise a trialkylsilyl triflate.

In certain embodiments, the present invention relates to a method of glycosylating a substrate, comprising the step of:
combining a compound represented by 1 and the attendant definitions with a substrate comprising an —OH, —NH—, or —SH moiety under reason conditions whereby said moiety of said substrate reacts with said compound represented by 1 and the attendant definitions to produce a glycosylated substrate, wherein said reaction conditions comprise trimethylsilyl triflate.

In certain embodiments, the present invention relates to a method of glycosylating a substrate, comprising the steps of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate, wherein said reaction conditions comprise trimethylsilyl triflate; and
purifying said glycosylated substrate.

In certain embodiments, the present invention relates to a method of glycosylating a substrate, comprising the step of:
combining a compound represented by 1 and the attendant definitions with a substrate comprising an —OH, —NH—, or —SH moiety under reaction conditions whereby said moiety of said substrate reacts with said compound represented by 1 and the attendant definitions to produce a glycosylated substrate, wherein said reaction conditions comprise trimethylsilyl triflate; and combining said glycosylated substrate with a compound represented by 1 and the attendant definitions under reaction conditions whereby an —OH, —NH—, or —SH moiety of said glycosylated substrate reacts with said compound represented by 1 and the attendant definitions to produce a glycosylated substrate comprising at least two sugar moieties derived from compounds represented by 1 and the attendant definitions, wherein said reaction conditions comprise trimethylsilyl triflate.

In certain embodiments, the present invention relates to a combinatorial method of synthesizing libraries of oligosaccharides, comprising the steps of:

dividing a sample of substrate into a plurality of portions;

reacting each portion of substrate with a single glycosyl donor; wherein not all portions of substrate are reacted with the same glycosyl donor, and the glycosyl donors are selected from the set consisting of glycals, glycosyl halides, glycosyl phosphates of claim 1, anhydrosugars, N-pentenyl glycosides, glycosyl sulfides, glycosyl sulfoxides, trichloroacetimidates, glycosyl sulfates, and glycosyl carboxylates; and purifying and combining the products of the previous step.

In certain embodiments, a method of the present invention produces said glycosylated product in greater than about 50% yield based on the compound represented by 1 and the attendant definitions. In certain embodiments, a method of the present invention produces said glycosylated product in greater than about 70% yield based on the compound represented by 1 and the attendant definitions. In certain embodiments, a method of the present invention produces said glycosylated product in greater than about 80% yield based on the compound represented by 1 and the attendant definitions. In certain embodiments, a method of the present invention produces said glycosylated product in greater than about 90% yield based on the compound represented by 1 and the attendant definitions.

Synthesis of Combinatorial Libraries of Carbohydrates

Two synthetic strategies for the preparation of combinatorial carbohydrate libraries are described. In one scheme, the glycosyl acceptor is attached to the solid support, while the other strategy uses a bidirectional synthesis scheme. Attachment of the glycosyl acceptor to the solid support holds several advantages. The glycosyl donor can be used in excess during the synthesis and side reactions involving the donor will not lead to chain termination. The non-reducing end of oligosaccharides has been shown to be involved in recognition phenomena. Using a support bound acceptor the non-reducing end of the growing oligosaccharide is exposed and allows for the screening of oligosaccharide ligands still attached to the support. Screening can alternatively be performed after release of the library from the support. Attachment of the non-reducing oligosaccharide terminus allows for the modification of the reducing end. When this approach is used, screening will be performed after cleavage of the products from the support.

Biologically important carbohydrate motifs have been found to be in many cases in the range of tetrasaccharides to decasaccharides. The libraries to be generated will be directed at entities of this size. Non-natural components will be incorporated into the synthesis scheme. Phosphorylation, sulfation or alkylation of uniquely exposed hydroxyl groups will generate even greater diversity of the libraries.

Libraries assembled by the acceptor bound strategy, which can be screened while still attached to the solid support, will be prepared by both the spatial separate synthesis as well as the split synthesis strategy.

Synthesis of the differentially protected monosaccharide building blocks poses a formidable task using traditional carbohydrate chemistry. Up to five hydroxyl groups have to be differentiated on each monomer and require lengthy protection and deprotection schemes. Glycals have proven extremely useful in the synthesis of complex oligosaccharides and glycopeptides and many differentially protected glycals are now commercially available. Danishefsky, S. J.; Bilodeau, M. T. *Angew. Chem. Int. Ed. Engl.* 1996, 35, 1380. The synthesis of selectively protected monosaccharide building blocks is greatly simplified since only three, rather than five, hydroxyls have to be distinguished. We have developed a straightforward, high yielding one-pot synthesis of glycosyl phosphates from glycal precursors. Glycosyl phosphates have also been shown to be highly effective and stereoselective in glycosylation reactions (see preceding sections).

Figure 6:
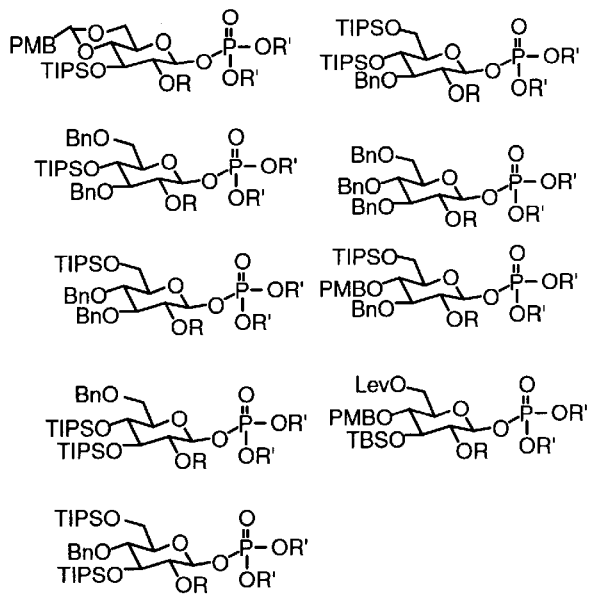
FIG. 6 depicts certain glycosyl phosphate donor building blocks for the synthesis of combinatorial carbohydrate libraries.
Figure 6:
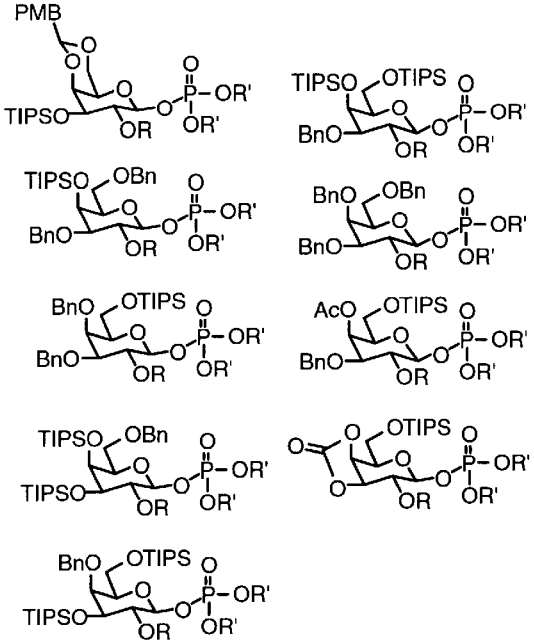
Figure 6:
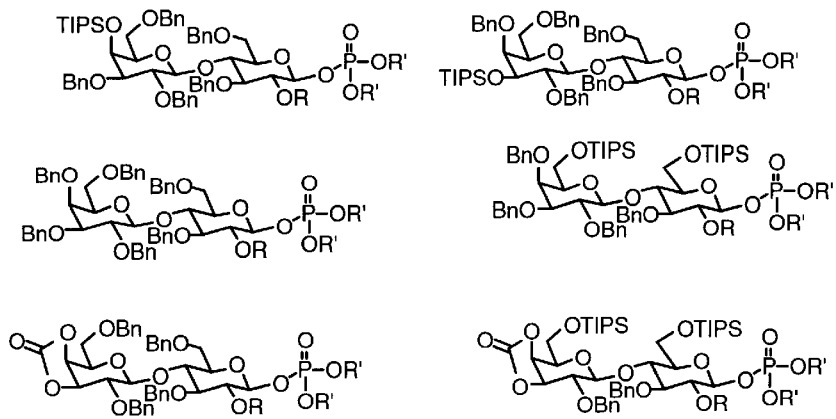
Figure 7:
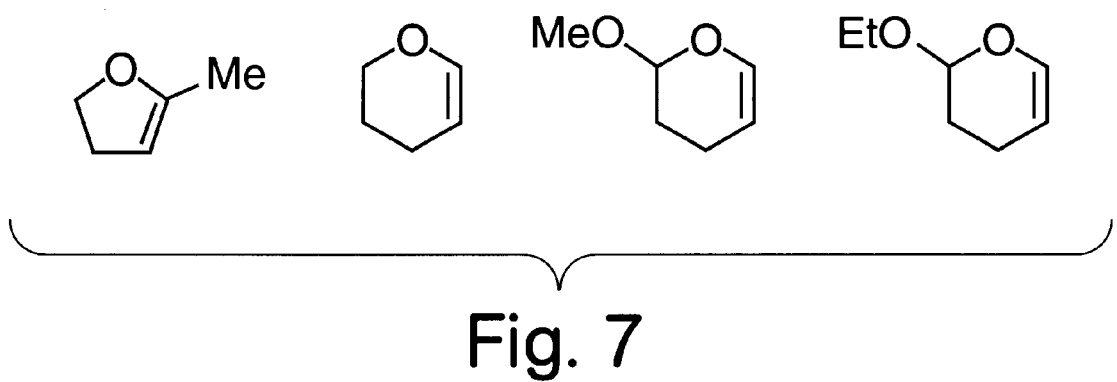
FIG. 7 depicts certain precursors for terminal building blocks for the acceptor bound synthesis strategy.

A variety of monosaccharide building blocks will be prepared by the procedures described above (FIG. 6). The protecting groups on these monomers can be varied depending upon the linker used for synthesis and many of the glycal precursors are either commercially available or can be rapidly prepared by differential protection. Besides carbohydrate building blocks other enol ethers may be employed as terminating building blocks in the preparation of libraries. Some examples of precursors for non-natural building blocks is shown in FIG. 7.

A host of different resins may be used for the synthesis of combinatorial libraries on the solid support including polystyrene and controlled pore glass supports. In order to be able to test polymer bound libraries, polyethylene glycol (PEG) polystyrene copolymers (TentaGel or ArgoGel) will be employed since they provide a solution-like environment for the bound ligands in the aqueous solution of the binding assays.

The linkers which connect the oligosaccharide to the polymer support will be chosen so that they are stable during the synthesis but can be selectively removed at the end of it. The oligosaccharide may be linked to the solid support either through a hydroxyl group or a C2-amino functionality. A variety of linkers is available for this task and will be chosen according to the synthetic task at hand.

Figure 8:
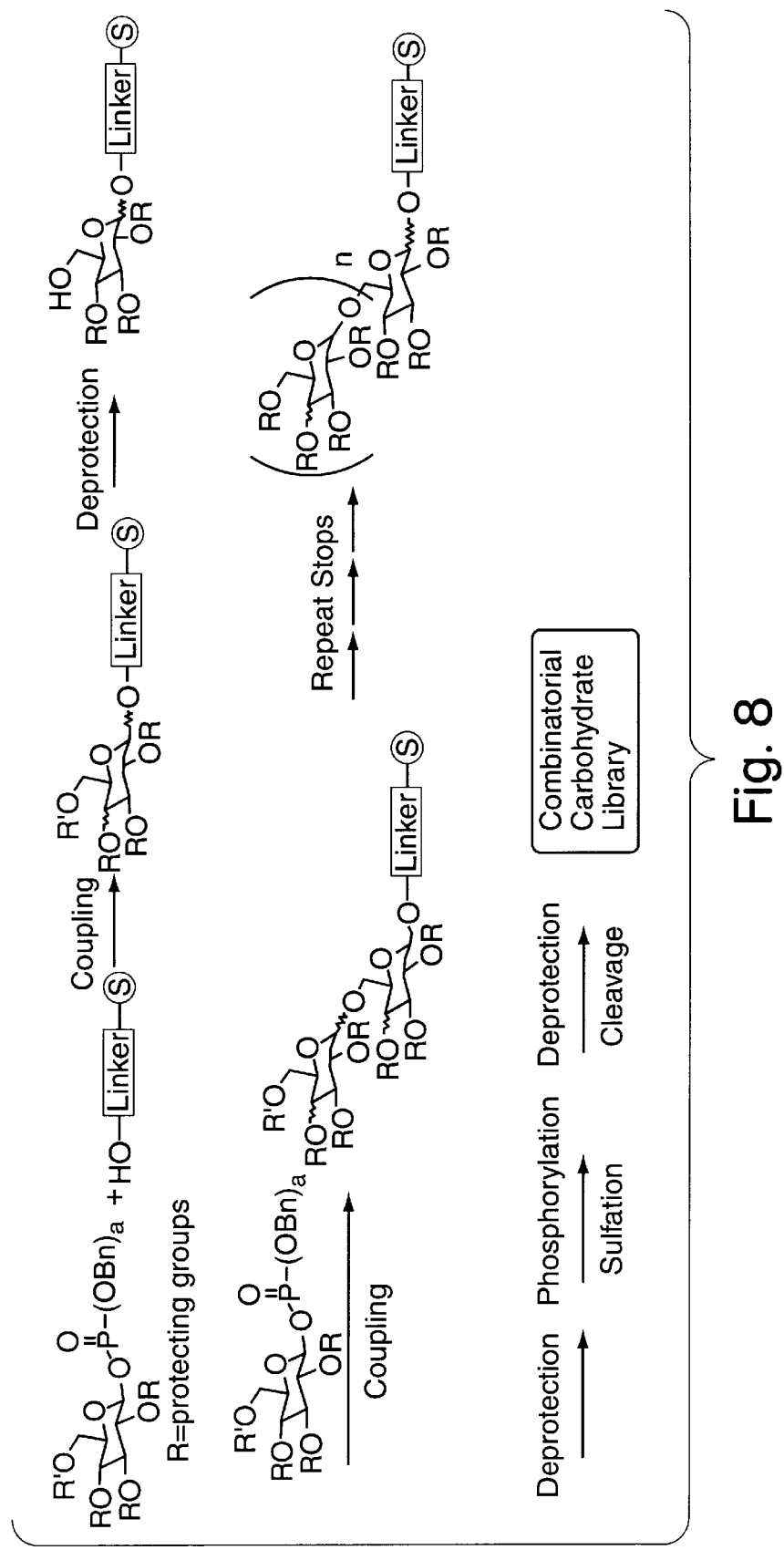
FIG. 8 depicts a synthetic protocol for the preparation of combinatorial carbohydrate libraries using the acceptor bound strategy.

The synthetic strategy for the preparation of combinatorial carbohydrate libraries utilizing a glycosyl acceptor bound to a solid support is outlined in FIG. 8. Elongation may be achieved through any exposed hydroxyl group of the support-bound acceptor. Besides carbohydrates other non-carbohydrate moieties may be introduced by reaction with the acceptor hydroxyl groups. In the acceptor bound synthesis this type of modification will be performed mainly at the end of the synthesis of linear combinatorial oligosaccharides or can be carried out at any point of the synthesis of branched oligosacchatide structures. Further modifications such as phosphorylation and sulfation are carried out at the end of the synthesis.

Removal of all protecting groups is achieved either while the libraries are still attached to the solid support, when screening is carried out on the beads or after cleavage from the solid support when screening is performed in solution.

Figure 9:
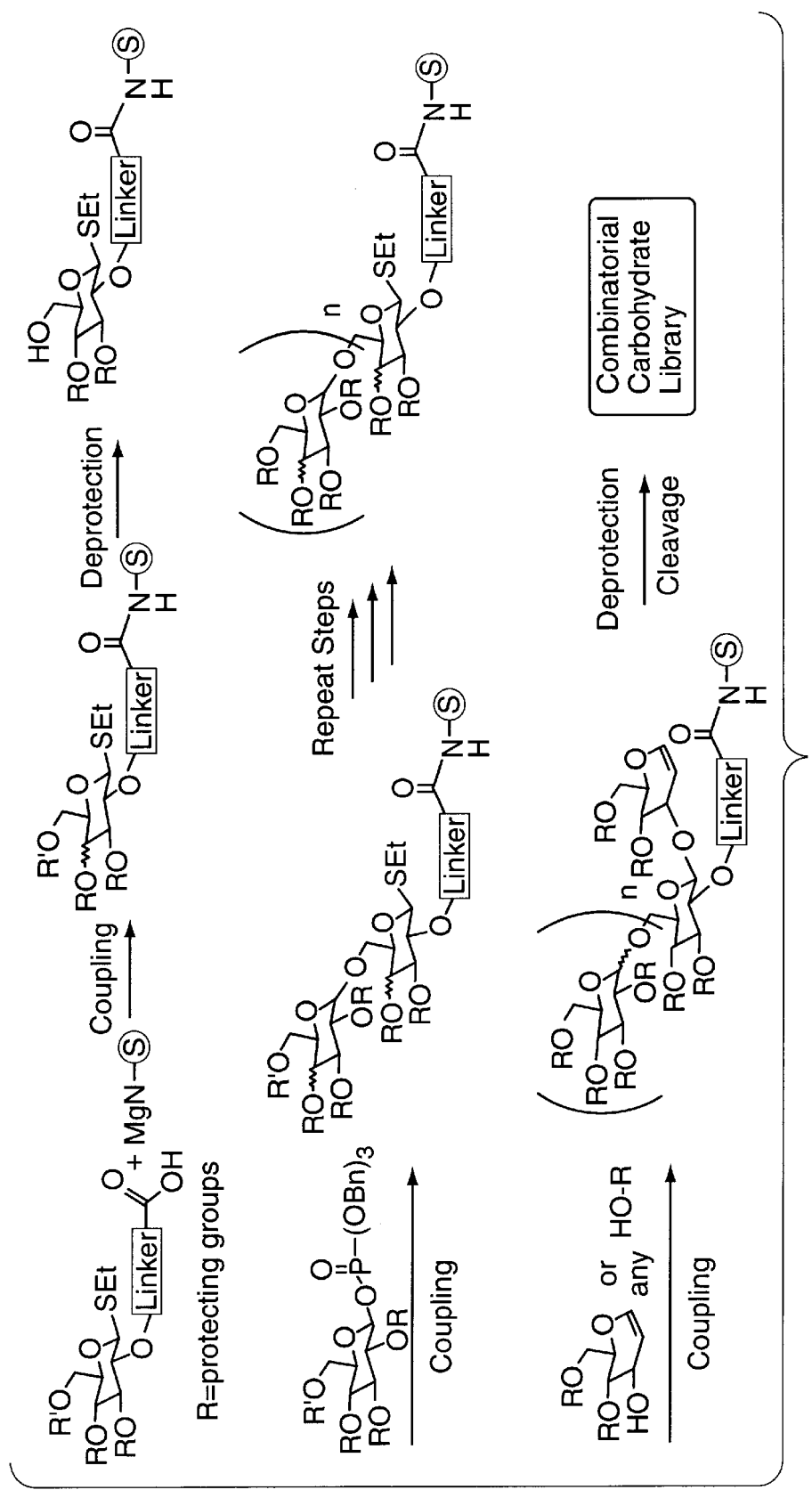
FIG. 9 depicts a synthetic protocol for the preparation of combinatorial carbohydrate libraries using a bi-directional strategy.

The bidirectional synthesis strategy is based on the principle of orthogonal glycosylation reactions. As described in the accompanying disclosure thioethyl glycosides are stable under conditions used to activate glycosyl phosphate glycosyl donors and may therefore function as glycosyl acceptors in coupling reactions. The first building block to be attached to the solid support is a thioethyl glycoside From this stage the protocol follows the strategy outlined above as the acceptor is attached to the solid support. After finishing assembly of combinatorial libraries in the acceptor bound direction, the thioethyl glycoside is activated to function as a glycosyl donor in the reaction with a solution based acceptor. The overall synthetic scheme is outlined in FIG. 9. This synthetic scheme will allow for the generation of combinatorial carbohydrate libraries of maximum diversity Phosphorylated and sulfated oligosaccharides have been identified as high-affinity ligands for carbohydrate binding proteins of the selectin family. Bertozzi, C. R. *Chemistry & Biology* 1995, 2, 703. Methods for the site-specific phosphorylation (Manning, D. D.; Bertozzi, C. R.; Rosen, S. D.; Kiessling, L. L. *Tetrahedron Lett.* 1996, 37, 1953) and sulfation (Lubineau, A.; Gallic, J. L.; Lemoine, R. *Bioorg. Med. Chem.* 1994, 2, 1143; Manning, D. D.; Bertozzi, C. R.; Pohl, N. L.; Rosen, S. D.; Kiessling, L. L. *J Org. Chem.* 1995, 60, 6252) of carbohydrates exist and will be applied to the solid support. Use of differentially protected monosaccharide building blocks will allow for the exposure of specific hydroxyls which can be phosphorylated or sulfated, thus resulting in greater diversity.

Combinatorial libraries containing oligosaccharides and carbohydrate based members, can in principle be screened in any high-throughput screen. Therefore, these libraries are attractive for many assay systems currently used by pharmaceutical companies.

Of specific interest is the identification of carbohydrate ligands of carbohydrate binding protein, lectins. Lectins are involved in many important signal transduction processes, including inflammation (selectins) and immune response (natural killer cell receptors). These screening experiments are expected to identify inhibitors of protein-carbohydrate interactions and potent therapeutic agents in a variety of applications.

Glycosyl phosphates combine the advantages of several of these glycosylation methods while avoiding most of the disadvantages. The differentially protected glycal precursors require only minimal protecting group manipulations and can be converted into glycosyl phosphates in a high yielding, straightforward one-pot procedure. Activation of the glycosyl phosphates occurs at very low temperatures using non-toxic activators and resulting in very high yields wind complete selectivity. The generation of combinatorial libraries using glycosyl phosphates will make use of these advantages and will allow facile access to libraries containing more diverse and more complex oligosaccharides and carbohydrate mimetics.

Combinatorial carbohydrate libraries hold a tremendous potential with regard to potential therapeutic applications. The key role complex oligosaccharides play in biological processes such as inflammation, immune resonse, cancer and fertilization makes them highly attractive therapeutic targets. The ability to create true oligosaccharide libraries has the potential to trigger a revolution in the area of biopharmaceuticals.

Definitions

For convenience, before further description of the present invention, certain terms employed in the specification, examples, and appended claims are collected here.

The terms "purify" means to increase through deliberate action the homogeneity of a compound, composition, preparation or solution.

The term "purified" refers to a compound, composition, preparation or solution whose homogeneity has been increased by purification. Typically, a purified compound, composition, preparation or solution has less than about 10% impurities, preferably less than about 5% impurities, and most preferably less than about 2% impurities.

The term "Lewis acid" is art-recognized and refers to an atom, compound or complex capable of accepting a pair of electrons from another atom, compound or complex.

The terms "glycosylated product" and "glycosylated substrate" are art-recognized and refer to the product of a reaction that covalently attached one or more sugar moieties to the substrate for said reaction.

The term "dioxirane" is art-recognized and refers to a three-membered ring which consists of two oxygen atoms and one carbon atom, wherein the carbon atom bears two substituents that render it tetrahedral.

The term "dimethyl dioxirane" refers to the compound below.

dimethyl dioxirane

The term "nucleophile" is recognized in the art, and as used herein means a chemical moiety having a reactive pair of electrons.

The term "electrophile" is art-recognized and refers to chemical moieties which can accept a pair of electrons from a nucleophile as defined above, or from a Lewis base. Electrophilic moieties useful in the method of the present invention include halides and sulfonates.

The tern "electron-withdrawing group" is reognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term "catalytic amount" is recognized in the art and means a substoichiometric amount of a reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "arylalkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that comprise a double or triple bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiment, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more rings in which two or more carbons are common to two adjoining rings (the rings are "fused") wherein at least one of the rings is aromatic, e.g., the other rings can be cycloalkyls, cycloalkenyls, cycloalkynyls, aryls and/or heterocyclyls.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms ore termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —NO$_2$; the term "halogen" designates —F, —Cl, —Br or —I; the term "sulfhydryl" means —SH; the term "hydroxyl" means -OH; and the term "sulfonyl" means —S$_2$—.

The terms "amine" and "amino" are art recognized and refer to both unsubstituted and substituted amines, e.g., a moiety that can be represented by the general formula:

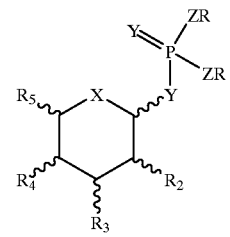

1 wherein R$_9$, R$_{10}$ and R'$_{10}$ each independently represent a hydrogen, an alkyl, an alkenyl, —(CH$_2$)$_m$R$_8$, or R$_9$ and R$_{10}$ taken together with the N atom to which they are attached complete a heterocycle having from 4 to 8 atoms in the ring structure; R$_8$ represents an aryl, a cycloalkyl, a cycloalkenyl, a heterocycle or a polycycle; and m is zero or an integer in the range of 1 to 8. In preferred embodiments, only one of R$_9$ or R$_{10}$ can be a carbonyl, e.g., R$_9$, R$_{10}$ and the nitrogen together do not form an imide. In even more preferred embodiments, R$_9$ and R$_{10}$ (and optionally R'$_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

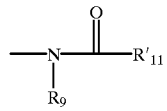

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

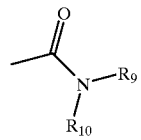

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethylthio, and the like.

The term "carbonyl" is art recognized and includes such moieties as can be represented by the general formula:

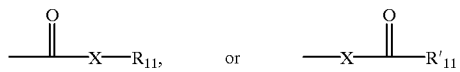

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

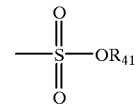

in which $R_{41}$ is an electron pair, hydrogen, alkyl, cycloalkyl, or aryl.

The term "sulfate" is art recognized and includes a moiety that can be represented by the general formula:

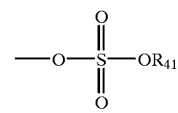

in which $R_{41}$ is as defined above.

The term "sulfonamido" is art recognized and includes a moiety that can be represented by the general formula

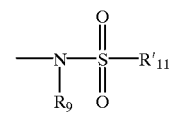

in which $R_9$ and $R'_{11}$ are as defined above.

The term "sulfamoyl" is art-recognized and includes a moiety that can be represented by the general formula:

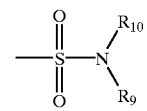

in which $R_9$ and $R_{10}$ are as defined above.

The terms "sulfoxido" or "sulfinyl", as used herein, refers to a moiety that can be represented by the general formula:

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

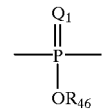

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

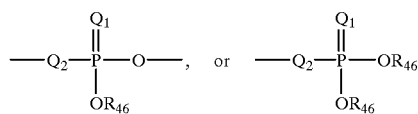

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

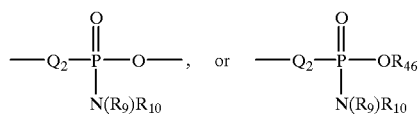

wherein $R_9$ and $R_{10}$ are as defined above, and $Q_2$ represents O, S or N.

A "phosphonamidite" can be represented in the general formula:

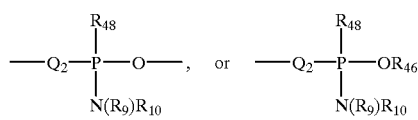

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any maimer by the permissible substituents of organic compounds.

A "polar solvent" means a solvent which has a dielectric constant (s) of 2.9 or greater, such as DMF, THF, ethylene glycol dimethyl ether (DME), DMSO, acetone, acetonitrile, methanol, ethanol, isopropanol, n-propanol, t-butanol or 2-metboxyethyl ether. Preferred solvents are DMF, DME, NMP, and acetonitrile.

A "polar, aprotic solvent" means a polar solvent as defined above which has no available hydrogens to exchange with the compounds of this invention during reaction, for example DMF, acetonitrile, diglyme, DMSO, or THF.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Reaction Conditions

The reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants, products and catalyst.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimedioxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethiformamide and the like, or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition Of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, derivativation with one or more of substituents of the aryl group.

Subsequent Transformations

A product synthesized by a method of the present invention may be either an end-product or an intermediate in a synthesis scheme. In cases where the product syntheized by a method of the present invention is an intermediate, the product may be subjected to one or more additional transformations to yield the desired end-product. The set of additional transformations contemplated comprises isomerizations, hydrolyses, oxidations, reductions, additions, eliminations, olefinations, functional group interconversions, transition metal-mediated reactions, transition metal-catalyzed reactions, bond-forming reactions, cleavage reactions, fragmentation reactions, thermal reactions, photochemical reactions, cycloadditions, sigmatropic rearrangements, electrocyclic reactions, chemoselective reactions, regioselective reactions, stereoselective reactions, diastereoselective reactions, enantioselective reactions, and kinetic resolutions. The invention expressly comprises use of a method of the present invention as a step—either initial, intermediate or final—in the synthesis of known or new pharmaceuticals, e.g., antivirals, antibiotics, and analgesics.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or sususpension; (3) topical application, for example, as a cream, ointment or spray applied to the skin; or (4) intravaginally or intarectally, for example, as a pessary, cream or foam.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water, (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J Pharm. Sci* 66:1–19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobroric, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamme, diethanolamine, piperazine and the like, (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated bydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofiryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agent and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monogtearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject co,pounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intravectally, for example, as a pessary, cream or foam.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Oreg., U.S.A., 1977).

Overview of Strategies and Methods of Combinatorial Chemistry

The subject complexes, and the reactions they catalyze, lend themselves to the creation of combinatorial libraries of compounds, including for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional method.

The art of combinatorial chemistry may be applied to the subject invention in a number of senses, including, but not limited to: the combinatorial synthesis of variegated libraries of metal-containing complexes that may be screened for the redox properties noted above; and the use of novel metal-containing complexes of the present invention as reagents in redox reactions carried out on combinatorial libraries of organic molecules.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No 5,288,514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lemer et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A) Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reuged in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82;5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S.P.A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated A in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) PNAS 89:5381–5383), and an example of such a library appeared the following year Needles et al. (1993) *PNAS* 90:10700–10704). A combinatorial library of nominally $7^7$ (=823,543) peptides composed of all combinations of Arg, Ghn, Phe, Lys, Val, D-Val and Thr (tree-letter amino acid code), each of which wag encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequenceable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobemzyl linker. This approach is Convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Ore Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates: second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention, and are not intended to limit the invention.

Example 1

Synthesis of Glycosyl Phosphates, and Glycosylation Reactions Utilizing Them

Existing protocols for the synthesis of anomeric phosphate-based glycosyl donors have relied on the phosphitylation or phosphorylation of an anomeric hydroxyl group following lengthy protection and deprotection protocols. Glycals, on the other hand, allow for the facile differential protection of the hydroxyl functionalities and have been shown to be versatile starting materials for the synthesis of oligosaccharides and natural products. We were able to demonstrate that glycosyl dithiophosphates as well as glycosyl phosphates could be efficiently prepared via a one-pot procedure. Conversion of glycals to anomeric phosphates was achieved by epoxidation of the glycal double bond with dimethyldioxirane (DMDO) to furnish the 1,2-anhydrosugar (Scheme C1). Opening of the epoxide with diethyl dithiophosphate furnished a 1:1 mixture of α and β anomeric phosphorodithioates C2 in 82% yield. Introduction of different ester protecting groups on the C2-hydroxyl group was straightforward and could be carried out without prior purification of the anomeric dithiophosphate. Anomeric phosphorodithioates are stable compounds that may be stored for several weeks at room temperature without decomposition.

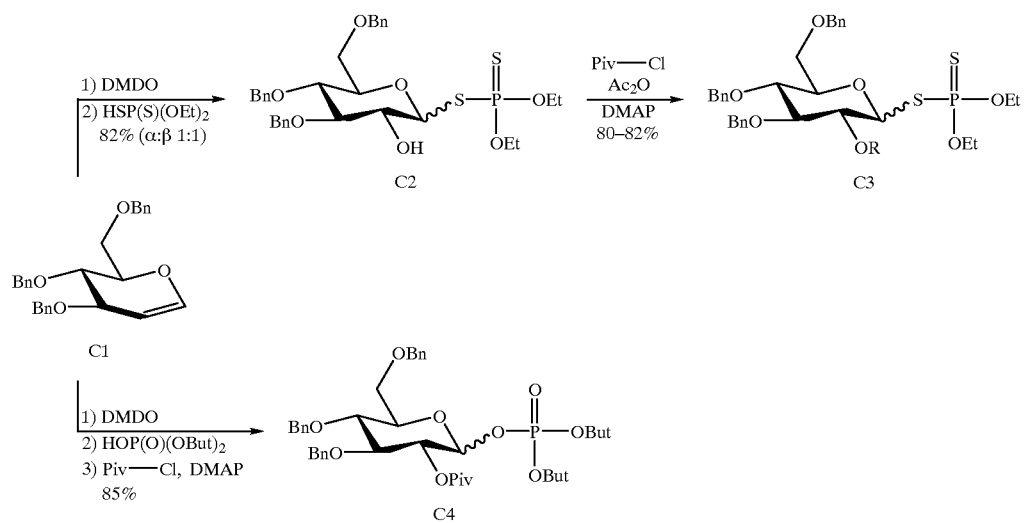

Scheme C1
Synthesis of glycosyl phosphates and glycosyl phosphorodithioates from glycal precursors (R = Piv or Ac).

This three step, 'one-pot' procedure was also successfully used to prepare a variety of differentially protected glycosyl phosphates (Scheme C1). Either α- or β-glycosyl phosphates could be prepared selectively by taking advantage of a strong solvent dependence of the epoxide opening. While reactions in toluene and dichloromethane produced preferentially β-phosphates, reactions in THF resulted almost exclusively in the formation of α-phosphates. Using this approach, differentially protected glucosyl, galactosyl and lactosyl phosphates were prepared. Introduction of participating groups in the C2 position by acylation in situ proved straightforward and high yielding. Silylation of the C2 hydroxyl to install a non-participating TES group was also feasible. The highly reactive β-phosphates were purified by filtration through a short plug of silica gel and could be stored at −20° C. for several weeks without decomposition, while α-phosphates could be stored for months at 4° C.

After having established a straightforward and high-yielding synthetic route for the preparation of differentially protected anomeric phosphates and phosphorodithioates, we evaluated the potential of these compounds as glycosylating agents. Activation of anomeric phosphorodithioates C3 with methyl triflate at room temperature required reaction times of 16 h and produced exclusively the β-glycosidic linkage by virtue of the participating pivaloyl ester functionality on C2. The yield as well as the rate of reaction were indistinguishable when either the α- or the β-phosphorodithioate was used. The coupling of C3 with a yuivty of glycosyl acceptors revealed that these novel glycosyl donors also selectively furnished the β-glucosidic linkage with hindered acceptors in good yield (see Scheme C2). Acid-sensitive glycal acceptors could successfully be accommodated in coupling reactions when a base such as di-tert-butylpyridine was included without requiring prolonged reaction times.

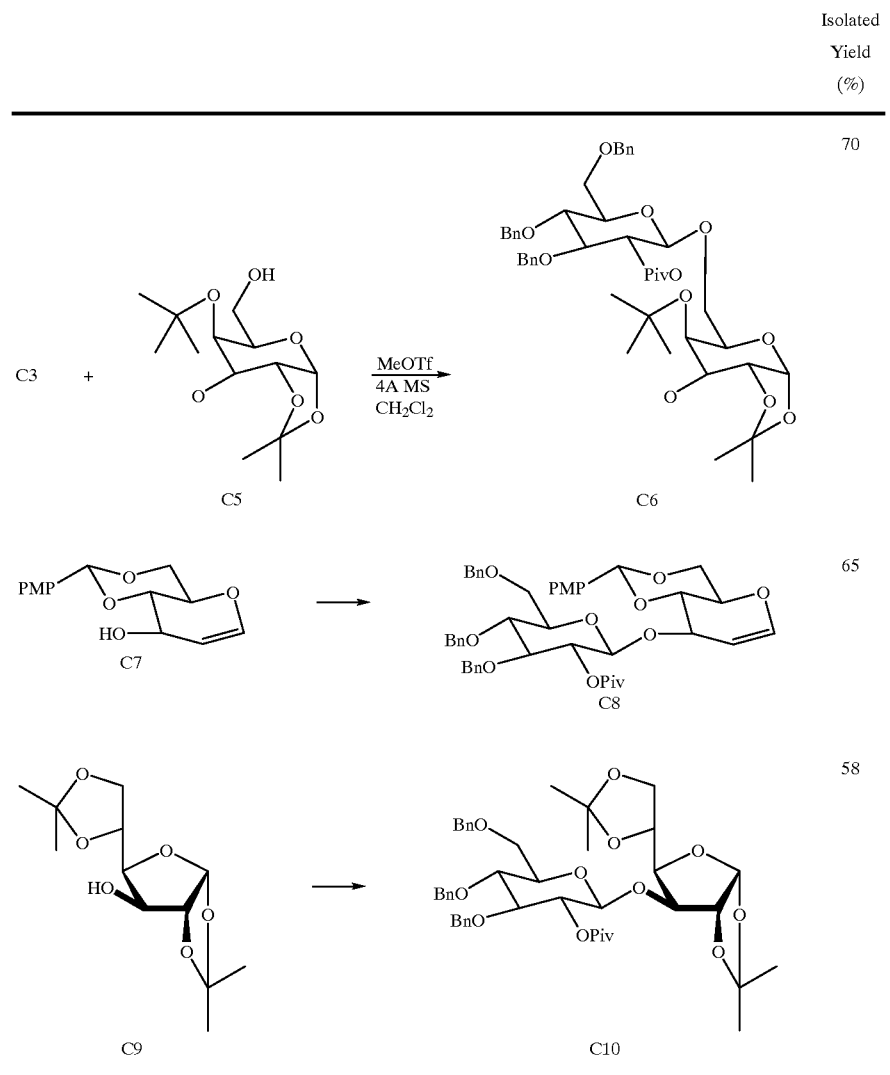

Scheme C2. Glycosylations using glycosyl phosphorodithioate donors.

While anomeric phosphorodithioates are useful new glycosylating agents, we were able to show that anomeric phosphates perform even better as glycosyl donors. Anomeric β-phosphates served as donors in the high yielding, selective formation of β-glycosidic linkages in only ten minutes upon activation with trimethylsilyl triflate (TMSOTf) at −78° C. (Scheme C3). Participation of the protecting group in the C2 position was not required for the selective formation of β-glycosidic linkages as a C2-TES protected donor C13 yielded exclusively the desired β-disaccharide. Primary and hindered secondary alcohols could be coupled in very high yields and reaction with ethanethiol resulted in the efficient conversion of glycosyl phosphate C4 into the corresponding thioethyl glycoside C16. The more stable α-phosphates acted as equally good glycosylating agents upon activation with TMSOTf at −20° C., while no reaction was observed at lower temperatures.

Scheme C3. Glycosyl Phosphates as glycosylating agents.
Glycosylations were carried out with 1.2 equiv. donor, 1.0 equiv. acceptor and 1.2 equiv. TMSOTf in dichloromethane at −78° C.

| Glycosyl Donor | Glycosyl Acceptor | Product | Yield |
|---|---|---|---|
| 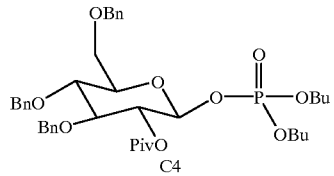 C4 | 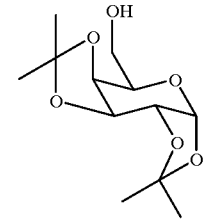 C5 | C6 | 94 |
| C4 | 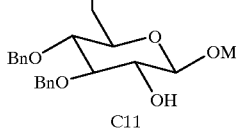 C11 | 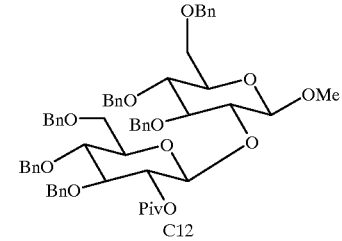 C12 | 83 |
| 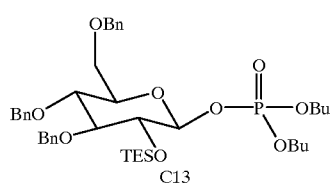 C13 | C5 | 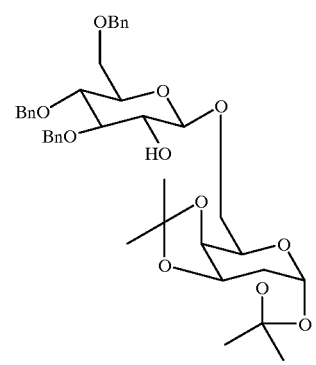 C14 | 71 |
| C4 |  C15 | 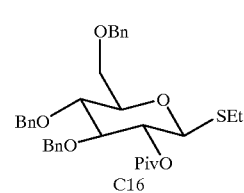 C16 | 90 |

The exclusive formation of β-glycosides independent of the anomeric configuration of the glycosyl donor and the use of non-participating groups in C2 suggests that upon activation of the glycosyl phosphato by TMSOTf, an anomeric α-triflate rather than a reactive oxonium ion intermediate is formed. Based on these observations we investigated the use of glycosyl phosphates for the preparation of β-mannosidic linkages. With hindered secondary alcohols as acceptors 88% disaccharide was obtained in a ratio of 3:1 in favor of the desired β-mannoside C17 when the reaction was carried out in dichloromothaic as a solvent, Interestingly, when the reaction was performed in the participating solvent acetonitrile, the α-mannoside C18 was obtained in a 5.5:1 ratio.

Scheme C4
Preparation of α- and β-mannosides.

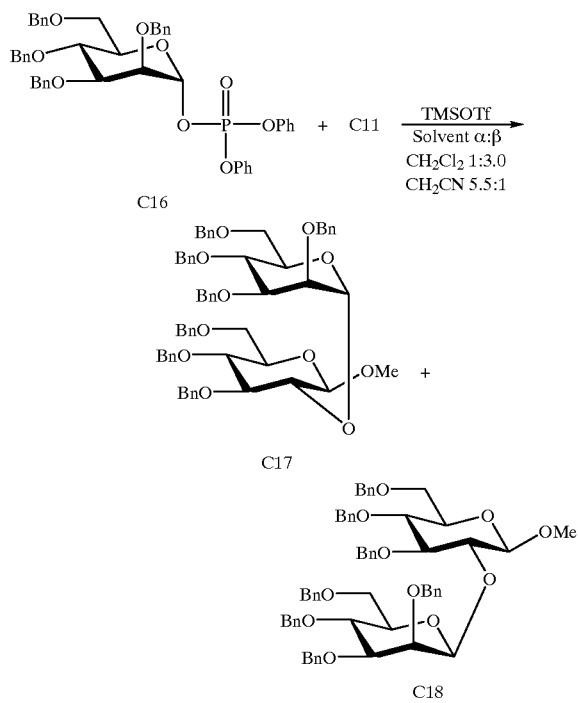

Given the high reactivity of β-glycosyl phosphates under conditions where thioethyl glycosides are completely stable, we developed an orthogonal coupling strategy minimizing protecting group manipulations (Scheme C5). Thioethyl mannoglycoside C19 was glycosylated using glycosyl phosphate C4 to yield 83% of disaccharide C20. Without any further manipulations, C20 was coupled with glycal acceptor C21 upon activationi with methyl triflate. The glycal double bond of trisaccharide C22 allows for further elongation by the glycal assembly method.

Scheme C5
Orthogonal glycosylations using glycosyl phosphates and thioglycosides.

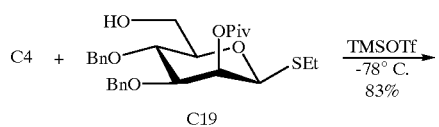

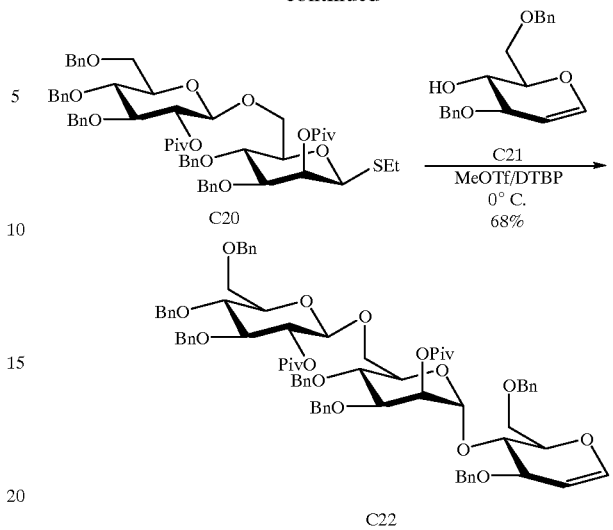

Example 2
Synthesis and Use of Glycosyl Phosphates as Glycosy Donors

Differentially protected glycosyl phosphates prepared by a straightforward synthesis from glycal precursors are used as powerful glycosyl donors. Activation of β-glycosyl phosphates by TMSOTf at −78° C. achieves the selective formation of β-glycosidic linkages in excellent yields with complete stereoselectivity. Reaction with thiols results in the conversion of glycosyl phosphates into thioglycosides in nearly quantitative yield. An orthogonal coupling strategy using glycosyl phosphate donors and thioethyl glycoside acceptors allows for the rapid synthesis of a trisaccharide.

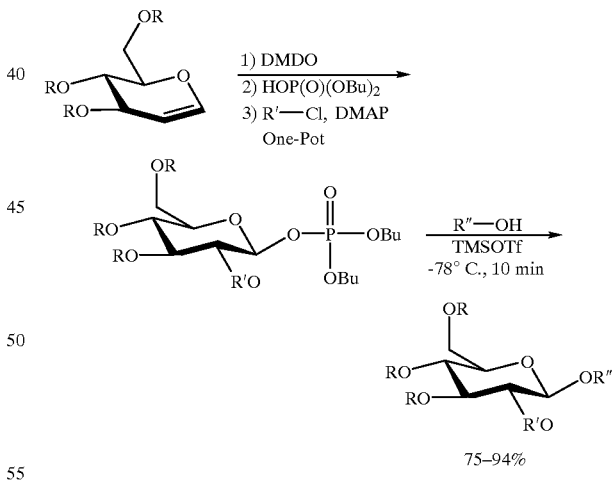

Complex glycoconjugates have been implicated in many cell-cell recognition events important in inflammation, immune response, and tumor metastasis.[1,2] Much effort has been devoted to the development of novel, powerful glycosylation reactions to facilitate access to defined, synthetic oligosaccharide and glycoconjugate structures.[3] A wide range of anomeric groups including most notably trichloroacetimidates,[4] thioethyl glycosides,[5] glycosyl sulfoxides,[6] fluorides,[7] and pentenyl glycosidese[8] have been explored as glycosyl donors. While these methods have proven very useful for the installation of a variety of glycosidic linkages, they still suffer in many cases from lengthly syntheses, long reaction times and the use of toxic activating agents. Thus, the need for the development of new, easily accessible glycosylating agents which may be coupled selectively and in high yield using non-toxic activators persists.

In biosynthesis, glycosyl transferases make use of glycosyl phosphates in the form of nucleotide diphosphate sugars (e.g. UDP-Glc) for the construction of glycosidic linkages.[9] In order to study these enzymatic reactions a number of synthetic approaches for the preparation of glycosyl phosphates have been developed.[10] While several phosphate analogs including phosphites,[11] phosphoramidates[12] and phosphorodithioates[13] have been employed as glycosyl donors in oligosaccharide synthesis, glycosyl phosphates have received surprisingly little attention for this application.[14]

We now report the efficient synthesis of glycosyl phosphates from glycals and their use as powerful glycosyl donors in the high yielding and completely selective construction of β-glycosidic linkages requiring very short reaction times.

TABLE

Synthesis of glycosyl phosphates from glycal precursors.[15]

| # | $R_1$ | $R_2$ | $R_3$ | $R_4$ | $R_5$ | $R_6$ | Solvent | % | β:α |
|---|---|---|---|---|---|---|---|---|---|
| 1 | Bn | H | OBn | Bn | Piv | Bn | $CH_2Cl_2$ | 74 | 10:1[a] |
|   |    |   |     |    |     |    | THF        | 71 | 1:10 |
|   |    |   |     |    |     |    | Toluene    | 84 | 17:1 |
| 2 | Bn | H | OBn | Bn | Piv | Bu | $CH_2Cl_2$ | 65 | 11:1 |
|   |    |   |     |    |     |    | THF        | 59 | 1:4 |
|   |    |   |     |    |     |    | Toluene    | 60 | 8:1 |
| 3 | Bn | OBn | H | Bn | Piv | Bu | $CH_2Cl_2$ | 57 | 4:1 |
| 4 | TIPS | H | OBn | Bn | Piv | Bn | $CH_2Cl_2$ | 65 | 1:0 |
| 5 | TIPS | H | OBn | Bn | Piv | Bu | THF | 70 | 1:1 |
| 6 | TBS | H | OPiv | Piv | Piv | Bu | $CH_2Cl_2$ | 75 | 1:0 |
| 7 | Bn | H | $OY^b$ | Bn | TES | Bu | $CH_2Cl_2$ | 71 | 1:0 |
| 8 | Bn | H | OBn | Bn | TES | Bu | THF | 79 | 2:1 |

[a]when the reaction was carried out at 0° C. a ratio of 4:1 (β:α) was observed;
[b]Y =2,3,4,6-tetra-O-benzyl-β-D-galactopyranoside-(1 → 4)-

A three step, 'one-pot' procedure was used to selectively prepare a variety of differentially protected glycosyl phosphates (Table 1). Conversion of a glycal into the 1,2-anhydrosugar by epoxidation with dimethyl dioxirane (DMDO) was followed by opening of the epoxide with a phosphoric acid and protection of the generated C2 hydroxyl group. We[13] and others[16] have recently described the syn thesis of anomeric phosphate derivatives using 1,2-anhydrosugars. A strong solvent dependence for the ratio of α and β glycosyl phosphates prepared by this method was observed While reactions in toluene and dichloromethane produced preferentially β phosphates, reactions in THF resulted almost exclusively in α phosphates (Table 1). Using this approach, differentially protected glycosyl (1,2,4-6,8), galactosyl (3) and lactonyl phosphates (7) were prepared. Introduction of participating groups in the C2 position by acylation proved straightforward and high yielding. Silylating of the C2 hydroxyl to install a non-participating TES group was also feasible, while introduction of a C2 TBS group failed. Efforts to equip the C2 position with a benzyl ether protecting group did not meet with success, but rather resulted in the isolation of benzyl C2 phosphate glycosides. Similar results had previously been observed in the dithiophosphate series.[13]

All α-phosphates as well as the C2-silyl β-glycosyl phosphates 7 and 8β were completely stable to silica column chromatography and could be stored at 4° C. for several weeks without decomposition. The phosphates 1β, 2β, and 5β, however, were more difficult to handle as they decomposed upon prolonged exposure to silica gel. Butylphosphates proved more stable than benzylphosphates and were easier to handle. Filtration through a short plug of silica gel yielded the pure desired compounds in all cases. Even these less stable β phosphates could be stored at −20° C. for several weeks without decomposition.

After having established a straightforward synthetic route for the preparation of differentially protected glycosyl phosphates we evaluated the performance of these compounds as donors in glycosylation reactions. Anomeric β-phosphates served as powerful donors in the high yielding, selective formation of β-glycosidic linkages in only ten minutes upon activation with trimethylsilyl triflate (TMSOTf at −78° C. (Table 2). Participation of the protecting group in the C2 position was not required for the selective formation of β-glycosidic linkages as the C2-TES protected donor 8β yielded exclusively the desired p-disaccharide 16 although the TES group was lost during the reaction. While primary and hindered secondary alcohols such as the C2 hydroxyl could be coupled in very good yields, tertiary acceptors failed to react. Efficient conversion of glycosyl phosphate 2β into the corresponding thioethyl glycoside 17 was achieved by coupling with ethanethiol.

The more stable α-phosphates could also serve as glycosyl donors upon activation with TMSOTf but requires higher temperatures for efficient activation. While no reaction was observed at −78° C., donor 2α was activated at −20° C. and coupled to galactosyl acceptor 9 to yield 87% of the desired β-disaccharide 13 within 10 minutes (Table 2). Couplings to more hindered acceptors and to thiols were also accomplished in good yields.

TABLE 2
Glycosylations with glycosyl phosphates and trimethylsilyl triflate
| Entry | Glycosyl Donor | Glycosyl Acceptor | Product | Yield |
|---|---|---|---|---|
| 1 | 2β | 9 | 13 | 94 |
| 2 | 2β | 10 | 14 | 83 |
| 3 | 5β | 9 | 15 | 82 |
| 4 | 8β | 9 | 16 | 71 |
| 5 | 2β | 11 | 17 | 90 |
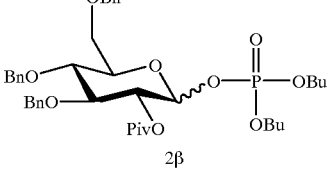

TABLE 2-continued

Glycosylations with glycosyl phosphates and trimethylsilyl triflate

| Entry | Glycosyl Donor | Glycosyl Acceptor | Product | Yield |
|---|---|---|---|---|
| 6[b] | 2α (structure shown) | 9 | 13 | 87 |
| 7[b] | 2α | 10 | 14 | 73 |
| 8[b] | 2α | 11 | 17 | 70 |

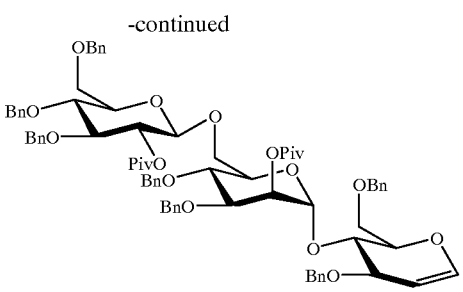

[a]Glycosylations were carried out with 1.2 equiv donor, 1.0 equiv acceptor and 1.2 equic TMSOTf in dichloromethane at −78° C.
[b]Reaction was carried out at −20° C.

Exclusive formation of β-glycosides using a non-participating group in C2 suggests that upon activation of the phosphate by TMSOTf, an anomeric triflate or a close ion pair of an moxonium ion intermediate is formed. Anomeic triflates have been proposed as intermediates in the formation of β-mannosides from thioglycosides by Crich.[17]

Since thioethyl glycosides were completely stable under the conditions used to activate β, glycosyl phosphates we investigated an orthogonal coupling strategy employing both glycosyl phosphates and thioethyl glycosides (Scheme 1). Thioethyl mannoglycoside 12 served as glycosyl acceptor in the reaction with glycosyl phosphate 2β to yield 83% of disaccharide 18. Without any further manipulations, 18 was used as a glycosyl donor and coupled to glycal acceptor 19 following previously described coupling conditions.[18] The glycal double bond of trisaccharide 20 allows for further elongation by the glycal assembly method.[19]

Scheme 1
Orthogonal glycosylation strategy using glycosyl phosphates and thioethyl glycosides

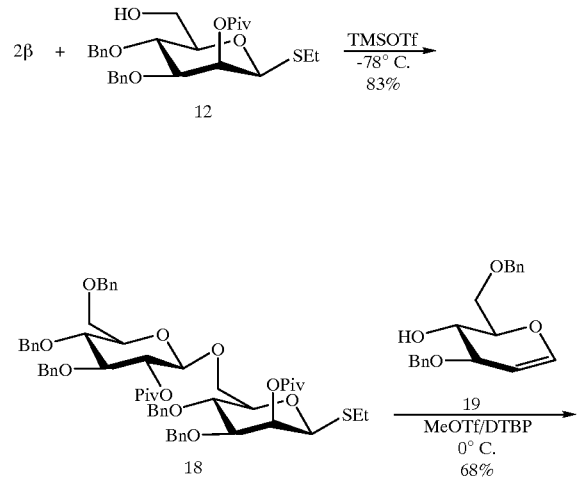

In summary, we have described the efficient synthesis of differentially protected glycosyl phosphates from glycals. We further demonstrated that α- and β-glycosyl phosphates serve as powerful glycosyl donors in the formation of β-glycosidic linkages in high yield and with complete selectivity. Efficient conversion of glycosyl phosphates into thioethyl glycosides was also achieved. Additionally, glycosyl phosphates and thioethyl glycosides were employed in the synthesis of a trisaccharide using an orthogonal glycosylation scheme, thus minimizing tedious protecting group manipulations.

REFERENCES & NOTES FOR EXAMPLE 2

(1) For reviews, see: (a) Varki, A. *Glycobiology* 1993, 3, 97. (o) Lee, Y. C.; Lee, R. T. *Acc. Chem. Res.* 1995, 28, 322.
(2) Chambers, W. H.; Brisette-Storkus, C. S. *Chemistry & Biology* 1995, 2, 429.
(3) For a review, see: Toshima, K.; Tatsuta, K. *Chem. Rev.* 1993, 93, 1503.
(4) For a review, see: Schmidt, R. R.; Kinzy, W. *Adv. in Carb. Chem. and Biochem.* 1994, 50,21.
(5) For a review, see: Garegg, P. J. *Adv. in Carb. Chem. and Biochem.* 1997, 52, 179.
(6) Kahne, D.; Walker, S.; Cheng, Y.; Van Engen, D. *J. Am. Chem. Soc.* 1989, 111, 6881.
(7) Mukaiyama, T.; Murai, Y.; Shoda, S. *Chem. Lett.* 1981, 431.

(8) Fraser-Reid, B.; Konradsson, P.; Mootoo, D. R.; Udodong, U. *J Chem. Soc. Chem. Comm.* 1988, 823.
(9) Heidlas, J. E.; Williams, K. W.; Whitesides, G. M. *Acc. Chem. Res.* 1992, 25, 307.
(10) (a) Inage, M.; Chaki, H.; Kusumoto, S.; Shiba, T. *Chem. Lett.* 1982, 1281. (b) Schmidt, R. R.; Stumpp, M. *Liebigs Ann. Chem.* 1984, 680. (c) Pale, P. ; Whitesides, G. M. *J Org. Chem.* 1991, 56, 4547. (d) Sabesan, S.; Niera, S, *Carb. Res.* 1992, 223, 169. (e) Sim, M. M.; Kondo, H.; Wong, C.-H. *J Am. Chem. Soc.* 1993, 115, 2260. (f) Boons, G.-J.; Burton, A.; Wyatt, P. *Synlett* 1996, 310.
(11) Kondo, H.; Aoki, S.; Ichikawa, Y.; Halcomb, R. L.; Ritzen, H.; Wong, C.-H. *J Org. Chem.* 1994, 59, 864.
(12) Hashimoto, S.; Sakamoto, H.; Honda, T.; Abe, H.; Nakamura, S.; Ikegami, S. *Tetrahedron Lett.* 1997, 38, 8969.
(13) Plante, O. J.; Seeberger, P. H. *J. Org. Chem.* 1998, 63, 9150.
(14) (a) Hashimoto, S.; Honda, T.; Ikegami, S. *J Chem. Soc., Chem. Commun.* 1989, 685. (b) Boger, D. L.; Honda, T. *J Am. Chem. goc.* 1994, 116, 5647. (c) Duynstee, H.I.: Wijsam, E. R.; van der Marel, G. A.; van Boom, J. H. *Synlett,* 1996, 313. (d) Bohm, G.; Waldmann, H. *Liebigs Ann.* 1996, 613.
(15) General Procedure: 1.0 equiv glycal, 1.5 equiv 0.08M dimethyldioxirane, 1.10 equiv dialkylphosphate, 1.5 equiv pivaloyl chloride and 3.0 equiv DMAP. All steps were carried out in dichloromethane unless noted otherwise.
(16) Timmers, C. M.; van Straten, N. C. R.; van der Marel, G. A.; van Boom, J. H. *J Carb.Chem.* 1998,17,471.
(17) Crich, D.; Sun, S. *J. Am, Chem. Soc.* 1998,120, 435.
(18) Seeberger, P. H.; Eckhardt, M.; Gutteridge, C.; Danishefsky, S. J. *J. Am. Chem. Soc.* 1997, 119, 10064.
(19) For a review, see: Danishefsky, S. J.; Bilodeau, M. T. *Angew. Chem., Int. Ed. Engl.* 1996, 35, 1380.

Example 3
Synthesis of Certain Glycosyl Phosphates
Synthesis of β-Enriched Glycosyl Phosphates. General Procedure A Suitably protected glycal (0.30 mmol) was dissolved in $CH_2Cl_2$ (2 mL) and cooled to 0° C. A 0.08M solution of dimethyldioxirane in acetone (6 mL, 0.45 mmol) was added and the reaction was stirred for 15 min. After the solvent was removed in a stream of $N_2$ and the remaining residue dried in vacuo for 15 min at 0° C., 5 mL $CH_2Cl_2$ were added. The solution was cooled to −78° C. for 15 min. A solution of dialkylphosphate (0.33 mmol) in 5 mL $CH_2Cl_2$ was added dropwise over 5 min. After complete addition, DMAP (0.15 mg, 1.2 mmol) and pivaloyl chloride (75 μL, 0.60 mmol) were added. The solution was warmed to room temperature over 1 h. The solvent was removed in a stream of $N_2$ and the residue chromatographed over silica gel to afford glycosyl phosphates as clear oils.

Synthesis of α-Enriched Glycosyl Phosphates. General Procedure B

Suitably protected glycal (0.30 mmol) was dissolved in $CH_2Cl_2$ (2 mL) and cooled to 0° C. A 0.08M solution of dimethyldioxirane in acetone (6 mL, 0.45 mmol) was added and the reaction was stirred for 15 min. After the solvent was removed in a stream of $N_2$ and the remaining residue dried in vacuo for 15 min at 0° C., 5 mL THF were added. The solution was cooled to −78° C. for 15 min. A solution of dialkylphosphate (0.33 mmol) in 5 mL THF was added dropwise over 5 min. After complete addition, DMAP (0.15 mg, 1.2 mmol) and pivaloyl chloride (75 μL, 0.60 mmol) were added. The solution was warmed to room temperature over 1 h. The solvent was removed in a stream of $N_2$ and the residue chromatographed over silica gel to afford the glycosyl phosphates as clear oils.

Synthesis of Dibenzyl 2-O-pivaloyl-3,4,6-tri-O-benzyl-β-D-glucopyranoside phosphate 1β, General Procedure A (74%, 10:1 β:α) $[\alpha]^{24}_D$:+45.4° (c 1.16, $CH_2Cl_2$); IR (thin film) 3010, 2941 1740, 1455, 1016 $cm^{-1}$; $^1$H-NMR ($CDCl_3$) δ7.37–7.25 (m, 23H), 7.18–7.16 (m, 2H), 5.35 (t, J=7.25 Hz, 1H), 5.24 (t, J=8.50 Hz, 1H), 5.11–5.09 (m, 2H), 5.03 (d, J=7.00 Hz, 2H), 4.82–4.77 (m, 2H), 4.72 (d, J=11.0 Hz, 1H), 4.58–4.52 (m, 2H), 4.44 (d, J=12.0 Hz, 1H 3.85 (t, J=9.50 Hz, 1H), 3.77–3.64 (m, 4H), 1.15 (s, 9H); $^{13}$C-NMR ($CDCl_3$) δ177.7, 138.3, 138.2, 138.0, 135.9, 135.8, 128.8, 128.7, 128.6, 128.0, 127.9, 127.6, 95.2, 95.1, 79.5, 76.8, 75.6, 75.3, 73.7, 72.7, 72.6, 69.7, 69.6, 69.5, 68.0, 38.9, 27.3; $^{31}$P-NMR ($CDCl_3$) δ−3.1; FAB MS m/z ($M^+$) calcd 794.3219, obsd 794.3224.

Synthesis of Dibenzyl 2O-pivaloyl-3,4,6-tri-O-benzyl-α-D-glucopyranoside phosphate 1α

General Procedure B (71%, 1:10 β:α) $[\alpha]^{24}_D$:+53.3°(c 1.44, $CH_2Cl_2$); IR (thin film) 2941, 2866, 1740, 1454, 1282 $cm^{-1}$; $^1$H-NMR ($CDCl_3$) δ7.37–7.25 (m, 23H), 7.18–7.16 (m, 2H), 5.95 (dd, J =3.50, 6.00 Hz, 1H), 5.09–5.05 (m, 4H), 4.97 (dt, J=3.50, 10.0 Hz, 1H), 4.82–4.79 (m, 3H), 4.58 (d, J=11.5 Hz, 1H), 4.53 (d, J=11.0 Hz, 1H), 4.44 (d, J=11.0 Hz, 1H), 4,02 (t, J=9.25 Hz, 2H), 3.81 (t, J=9.50 Hz, 1H), 3.69 (dd, J=3.50, 12.5 Hz, 1H), 3.50 (dd, J=1.50, 11.0 Hz, 1H), 1.18 (s, 9H); $^{13}$C-NMR ($CDCl_3$) δ177.7, 138.3, 138.2, 138.0, 135.9, 135.8, 128.8, 128.7, 128.6, 128.0, 127.9 127.6, 95.2, 95.1, 79.5, 76.8, 75.6, 75.3, 73.7, 72.7, 72.6, 69.7, 69.6, 69.5, 68.0, 38.9, 27.3; $^-$P-NMR ($CDCl_3$) δ−1.8; FAB MS m/z ($M^+$) calcd 794.3219, obsd 794.3216.

Synthesis of Dibutyl 2-O-pivaloyl-3,4,6-tri-O-benzyl-β-D-glucopyranoside phosphate 2β

General Procedure A (65%, 11:1 β:α) $[\alpha]^{24}_D$:−1.9° (c 1.50, $CH_2Cl_2$); IR (thin film) 2946, 1740, 1454, 1282, 1016 $cm^{-1}$; $^1$H-NMR ($CDCl_3$) δ7.33–7.25 (m, 13H), 7.16–7.14 (m, 2H), 5.24 (t, J=7.25 Hz, 1H), 5.17 (t, J=8.50 Hz, 1H), 4.80–4.75 (m, 2H), 4.70 (d, J=11,0 Hz, 1H) 4,69–4.54 (m, 2H), 4.51 (d, J=11.0 Hz, 1H), 4.08–4.00 (m, 4H), 3.82 (t, J=9.50 Hz, 1H), 3.78–3.70 (m, 3H), 3.64–3.61 (m, 1H), 1.64–1.59 (m, 4H), 1.40–1.34 (m, 4H), 1.20 (s, 9H), 0.96–0.88 (m, 6H); $^{13}$C-NMR ($CDCl_3$) δ177.2, 138.2, 138.1, 128.7, 128.3, 128.2, 128.1, 128.0, 127.6, 97.0, 96.5, 83.1, 76.2, 75.9, 73.9, 73.3, 68.4, 68.2, 68.1, 39.2, 32.7, 26.9, 19.1, 14.0; $^{31}$P-NMR ($CDCl_3$) δ−2.2; FAB MS m/z ($M^+$) calcd 726.3532, obsd 726.3537.

Synthesis of Dibutyl 2-O-pivaloyl-3,4,6-tri-O-benzyl-α-D-glucopyranoside phosphate 2α

General Procedure B (59%, 1:4 β:α) $[\alpha]^{24}_D$:+50.5° (c 0.63, $CH_2Cl_2$); IR (thin film) 2960, 2872, 1736, 1454, 1282 $cm^{-1}$; $^1$H-NMR ($CDCl_3$) δ7.35–7.27 (m, 13H), 7.18–7.15 (m, 2H), 5.85 (dd, J=1.75, 6.35 Hz, 1H), 4.99–4.97 (m, 1H), 4.83–4.80 (m, 3H), 4.63 (d, J=11.5 Hz, 1H), 4.56–4.50 (m, 3H), 4.10–4.02 (m, 5H), 3.86–3.79 (m, 2H), 3.68 (d, J=11.0 Hz, 1H), 1.86–1.61 (m, 4H), 1.44–1.36 (m, 4H), 1.24 (s, 9H), 0.97–0.91 (m, 6H); $^{13}$C-NMR ($CDCl_3$) δ177,7 138.3, 138.1, 138.0, 128.6, 128.5, 128.3, 128.2, 128.1, 128.0, 127.9, 127.7, 127.6, 94.7, 94.6, 79.5, 75.6, 75.4, 73.7, 72.7, 72.6 68.2 3 68.0 67.9 67.8 39.0, 32.5, 32.4, 27.3, 18.8, 13.8; $^{31}$P-NMR ($CDCl_3$) δ−2.5; FAB MS m/z ($M^+$) calcd 726.3532, obsd 726.3537.

Synthesis of Dibutyl 2-O-pivaloyl-3,4,6-tri-O-benzyl-β-D-galactopyranoside phosphate 3β

General Procedure A (57%, 4:1 β:α) $[\alpha]^{24}_D$:+7.7° (c 0.64, $CH_2Cl_2$); IR (thin film) 2960, 2872, 1740, 1454, 1277 $cm^{-1}$; $^1$H-NMR ($CDCl_3$) δ7.36–7.25 (m, 15H), 5.49 (dd, J=8.00, 10.0 Hz, 1H), 5.20 (t, J=7.50 Hz, 1H), 4.92 (d, J=11.5 Hz, 1H), 4.66 (d, J =12.0 Hz, 1H), 4.56 (d, J=11.5 Hz, 1H), 4.47–4.41 (m, 21), 4.05–3.96 (m, 5H), 3.73 (t, J=6.50 Hz, 1H), 3.64 (t, J=7.00 Hz, 1H), 3.60–3.57 (m, 3H), 1.64–1.56 (m, 4H), 1.41–1.32 (m, 4H), 1.20 (s, 9H), 0.93–0.87 (m, 6H); $^{13}$C-NMR (CDCl$_3$) δ177.3, 138.6, 138.0, 137.8, 128.8, 128.7, 128.5, 128.2, 128.1, 128.0, 127.6, 97.4, 80.7, 74.9, 74.4, 73.8, 72.8, 72.6, 71.29 71.1, 68.3, 68.1, 68.0, 39.2, 32.4, 32.3, 27.5, 18.9, 13.9; $^{31}$P-NMR (CDCl$_3$) δ–2.2; FAB MS m/z (M$^+$) calcd 726.3532, obsd 726.3531.

Synthesis of Dibutyl 2-O-pivaloyl-3,4,6-tri-O-benzyl-α-D-galactopyranoside phosphate 3α

General Procedure B (57%, 4:1 β:α) $[\alpha]^{24}_D$:+65.4° (c 2.41, CH$_2$Cl$_2$); IR (thin film) 2960, 2872, 1734, 1454 cm$^{-1}$; $^1$H-NMR (CDCl$_3$) δ7.36–7.25 (m, 15H), 5.84 (dd, J=3.60, 6.00 Hz, 1H), 5.41 (dt, J=3.30, 7.20 Hz, 1H), 4.96 (d, J=11.40 Hz, 1H), 4.70 (s, 2H), 4.56 (d, J=11.40 Hz, 1H), 4.43 (d, J=1.80 Hz, 2H), 4.19 (t, J=6.30, 1H), 4.09–3.97 (m, 6H), 3.63–3.51 (m, 2H), 1.66–1.57 (m, 4H), 1.43–1.29 (m, 4H), 1.24 (s, 9H), 0.94–0.88 (m, 6H); $^{13}$C-NMR (CDCl$_3$) δ177.8, 138.4, 138.1, 137.9, 128.6, 128.5, 128.4, 128.3, 128.2, 128.0, 127.9, 127.8, 127.5, 95.4, 95.3, 76.4, 75.0, 74.2, 73.7, 72.9, 71.5, 70.0, 69.9, 68.5, 68.0, 67.9, 67.8, 39.0, 32.5, 32.4, 27.4, 18.8, 13.8; $^{31}$P-NMR (CDCl$_3$) δ–2.3; FAB MS m/z (M) calcd 726.3532, obsd 726.3536.

Dibenzyl 3,4-di-O-benzyl-2-O-pivaloyl-6-O-triisopropylsilyl-β-D-glucopyranoside phosphate 4

General Procedure A (65%, 1:0 β:α) $[\alpha]^{24}_D$:+32.90 (c 1.12, CH$_2$Cl$_2$); IR (thin film) 2941, 2866, 1740, 1455, 1127cm$^{-1}$; $^1$H-NMR (CDCl$_3$) δ7.36–7.26 (m, 20H),5.33 (t, J=7.75Hz,1H),5.16 (t, J=8.75 Hz, 1H), 5.07 (d, J=7.50 Hz, 2H), 4.99 (d, J=7.00 Hz, 1H), 4.81 (d, J=10.5 Hz, 2H), 4.75–4.69 (m, 2H), 4.02–3.95 (m, 2H), 3.90 (t, J =9.25 Hz, 1H), 3.75 (t, J=9.00 Hz, 1H), 3.51–3.49 (m, 1H), 1.14 (s, 9H), 1.03 (s, 21H); $^{13}$C-NMR (CDCl$_3$) δ177.2, 138.2, 138.1, 128.1, 128.0, 127.8, 127.6, 97.2, 83.0, 75.4, 75.2, 73.2, 73.1, 69.7, 69.5, 67.3, 62.2, 39.0, 18.2, 12.1; $^{31}$P-NMR (CDCl$_3$) δ–2.8; FAB MS m/z (M$^+$) calcd 860.4084, obsd 860.4080.

Synthesis of Dibutyl 3,4di-O-benyl-2-O-pivaloyl-6-O-triisopropylsilyl-β-D-glucopyranoside phosphate 5β

General Procedure A (70%, 1:1 β:α) $[\alpha]^{24}_D$:–9.1° (c 2.79, CH$_2$Cl$_2$); IR (thin film) 2960, 2866, 1742, 1462, 1396 cm$^{-1}$; $^1$H-NMR (CDCl$_3$) δ7.38–7.21 (m, 10H), 5.24 (t, J=6.90Hz, 1H), 5.10 (t, J=9.00, 1H), 4.78 (t, J=12.00 Hz, 2H), 4.71 (t, J=10.8 Hz, 2H), 4.12–3.94 (m. 6H), 3.87 (t, J=9.30 Hz, 1H), 3.72 (t, J=9.30 Hz, 1H), 3.48 (d, J=9.90 Hz, 1H), 1.65–1.56 (m, 4H). 1.20 (s, 9H), 1.07 (s, 21H); $^{13}$C-NMR (CDCl$_3$) δ177.0, 138.2, 128.6, 128.4, 128.2, 128.0, 127.8, 127.5, 96.8, 83.0, 75.1, 73.2, 68.0, 62.3, 39.0, 32.4, 27.3, 18.8, 13.8, 12.1; $^{31}$P-NMR (CDCl$_3$) δ–2.56; FAB MS m/z (M$^+$) calcd 792.4397, obsd 792.4392.

Synthesis of Dibutyl 3,4-di-O-benzyl-2-O-pivaloyl-6-O-triisopropylsilyl-α-D-glucopyranoside phosphate 5α

General Procedure B (70%, 1:1 β:α) $[\alpha]^{24}_D$:+10.8° (c 1.00, CH$_2$Cl$_2$); IR (thin film) 2959, 2866, 1737, 1460, 1363 cm$^{-1}$; $^1$H-NMR (CDCl$_3$) δ7.38–7.19 (m, 10H), 5.78 (dd, J=6.25, 3.00 Hz, 1H), 4.86 (t, J=10.0 Hz, 1H), 4.80 (t, J=12.0 Hz, 2H), 4.74 (t, J=10.0 Hz, 1H), 4.11–3.92 (m, 6H), 3.92–3.82 (m, 3H), 1.70–1.58 (m, 4H), 1.44–1.32 (m, 4H), 1.21 (s, 9H) 1.05 (m, 21H), 0.95–0.88 (m, 6H); $^{13}$C-NMR (CDCl$_3$) δ177.8, 138.4, 128.6, 127.9, 94.8, 79.3, 75.4, 72.7, 67.8, 61.8, 38.9, 32.5, 27.3, 18.8, 18.5, 13.7, 13.1; $^{31}$P-NMR (CDCl$_3$) δ–2.45; FAB MS m/z (M$^+$) calcd 792.4397, obsd 792.4394.

Synthesis of Dibutyl 6-O-tert-butyldimethylsilyl-2,3,4-tri-O-pivaloyl-β-D-glucopyranoside phosphate 6

General Procedure A (75%, 1:0 β:α) $[\alpha]^{24}_D$:+13.10° (c 1.00, CH$_2$Cl$_2$); IR (thin film) 2961, 2874, 1746, 1479, 1397 cm$^{-1}$; $^1$H-NMR (CDCl$_3$) δ5.29 (t, J=9.50 Hz, 1H), 5.18 (t, J=9.50 Hz, 1H), 5.09 (t, J=8.50 Hz, 1H), 4.14–3.94 (m, 5H), 3.74–3.62 (m, 4H), 1.64–1.57 (m, 4H), 1.42–1.31 (m, 4H), 1.14 (s, 9H), 1.13 (s, 9H), 1.11 (s, 9H), 0.96–0.84 (m, 6H), 0.86 (s, 9H), 0.02 (s, 3H), 0.01 (s, 3H); $^{13}$NMR (CDCl$_3$) δ177.2, 176.7, 176.2, 96.6, 75.6, 72.5, 68.1, 31.7, 38.9, 32.3, 27.3, 25.9, 18.4, 13.7, –5.2; $^{31}$P-NMR (CDCl$_3$) δ–3.21; FAB MS m/z (M$^+$) calcd 754.4452, obsd 754.4455.

Synthesis of 2-O-Triethylsilyl Glycosyl Phosphates. General Procedure C

Suitably protected glycal (0.30 mmol) was dissolved in CH$_2$Cl$_2$ (2 mL) and cooled to 0° C. A 0.08M solution of dimethyldioxirane in acetone (6 mL, 0.45 mmol) was added and the reaction was stirred for 15 min. After the solvent was removed in a stream of N$_2$ and the remaining residue dried in vacuo for 15 min at 0° C., 5 mL THF were added. To the reaction vessel was added a solution of dialkylphosphate (0.33 mmol) in 5 mL THF dropwise over 5 min. at 0° C. After stirring for 10 min, imidazole (71 mg, 1.05 mmol) and triethylsilylchloride (126 μL, 0.75 mmol) were added. The solution was warmed to room temperature for 2 h. The reaction mixture was diluted with EtOAc (50 mL) and washed with a saturated NaHCO$_3$ solution, brine and water. After back extraction of the aqueous layers with 2×50 mL EtOAc, the organics were dried over NA$_2$SO$_4$ ana concentrated. The crude product was purified by flash silica column chromatography to afford 2-O-triethylsilylglycosyl phosphates.

Synthesis of Dibutyl 2,3,4,6-tetra-O-benzyl-β-D-galactopyranoside-(→4)-3,6-di-O-benzyl-2-O-triethylsilyl-β-D-glucopyranoside phosphate 7

General Procedure C (71%, 1:0 β:α) $[\alpha]^{24}_D$:+5.4° (c 1.06, CH$_2$Cl$_2$); IR (thin film) 2957, 2874, 1454, 1362, 1279 cm$^{-1}$; $^1$H-NMR (CDCl$_3$) δ7.33–7.15 (m, 30H), 5.17 (d, J=18.0 Hz, 1H), 5.00 (dd, J=5.85, 6.00 Hz, 1H), 4.90 (d, J=12.0 Hz, 1H), 4.80–4.60 (m, 5H), 4.50–4.28 (m, 5H), 4.19 (d, J=12.0 Hz, 1H), 4.11–3.98 (m, 6H), 3.86–3.82 (m, 2H), 3.74–3.56 (m, 3H), 3.49–3.25 (m, 5H), 1.66–1.56 (m, 4H), 1.43–1.31 (m, 4H), 0.97–0.85 (m, 15H), 0.64–0.56 (m, 6H); $^{C-NMR}$(CDCl$_3$) δ139.6, 139.3, 138.9, 138.8, 138.4, 138.3, 128.6, 128.5, 128.3, 128.2, 128.1, 128.0, 127.9, 127.8, 127.7, 127.6, 127.5, 126.9, 102.9, 99.6, 99.5, 83.5, 82.7, 80.1, 76.3, 75.7, 75.6, 74.9, 74.8, 73.8, 73.6, 73.4, 73.3, 72.8, 68.3, 68.1, 67.8, 67.7, 32.5, 32.4, 18.9, 13.9, 7.1, 5.2; $^{31}$P-NMR (CDCl$_3$) δ–2.0; FAB MS m/z (M$^+$) calcd 1188.5759, obsd 1188.5756.

Synthesis of Dibutyl 3,4,6-tri-O-benzyl-2-O-triethylsilyl-β-D-glucopyranoside phosphate 8β

General Procedure C (79%, 2:1 β:α) $[\alpha]^{24}_D$: –8.3° (c 4.39, CH$_2$Cl$_2$); IR (thin film) 2976, 2870, 1460, 1130 cm$^{-1}$; $^1$H-NMR (CDCl$_3$) δ7.37–7.25 (m, 13H), 7.12–7.09 (m, 2H), 5.02 (dd, J=6.00, 7.50 Hz, 1H), 4.93–4.86 (m, 2H), 4.75 (d, J=11.0 Hz, 1H), 4.61–4.50 (m, 3H) 4.13–4.08 (m, 4H), 3.75–3.67 (m, 4H), 3.61–3.58 (m, 1H), 3.55 (t, J=8.57 Hz, 1H), 1.69–1.60 (m, 4H), 1.45–1.38 (m, 4H), 1.00–0.89 (m, 15H), 0.68 (q, J=8.00 Hz, 6H); $^{13}$C-NMR (CDCl$_3$) δ139.0, 138.3, 138.2, 128.7, 128.6, 128.2, 128.1, 128.0, 127.6, 127.5, 99.5, 85.8, 77.9, 75.8, 75.6, 75.5, 75.4, 75.2, 73.8, 68.8, 68.0, 67.9, 32.6, 32.5, 19.0, 14.0, 13.9, 7.2, 5.3; $^{31}$P-NMR(CDCl$_3$) δ–1.4; FAB MS m/z (M) calcd 756.3822, obsd 756.3822.

Synthesis of Dibutyl 3,4,6-tri-O-benzyl-2-O-triethylsilyl-α-D-glucopyranoside phosphate 8α

General Procedure C (79%, 2.1 β:α) $[\alpha]^{24}_D$:+44.1° (c 1.50, CH$_2$Cl$_2$); IR (thin film) 2976, 2870, 1460, 1130 cm$^{-1}$H-NMR (CDCl$_3$) δ7.37–7.26 (m, 13H), 7.10–7.09 (m, 2H), 5.65 (dd, J=2.50, 6.25 Hz, 1H), 4.93 (d, J=11.5 Hz, 1H), 4.83–4.79 (m, 2H), 4.62 (d, J=12.0 Hz, 1H), 4.51–4.47 (m, 2H), 4.12–3.98 (m, 5H), 3.84–3.70 (m, 4H), 3.65 (d, J=10.0 Hz, 1H), 1.70–1.60 (m, 4H), 1.45–1.34 (m, 4H), 1.02–0.89 (m, 15H), δ0.67 (q, J=8.00 Hz, 6H); $^{13}$C-NMR (CDCl$_3$) δ138.9, 138.3, 138.0, 128.6, 128.5, 128.2, 128.0, 127.9, 127.7, 127.6, 97.9, 97.8, 82.2, 75.8, 75,3, 73.8, 73.4, 73.3, 72.5, 68.3, 67.8, 67.6, 67.5, 32.5, 32.4, 18.9, 18.8, 13.8, 7.0, 5.1; $^{31}$P-NMR (CDCl$_3$) δ–2.3; FAB MS m/z (M$^+$) calcd 756.3822, obsd 756.3823.

Example 4
Various Glycosylation Reactions Utilizing Glcosyl Phosphates
General Procedure D β-Phosphate glycosyl donor (0.12 mmol) and glycosyl acceptor (0.10 mmol) were combined and azeotropically dried with toluene (3×5 mL) followed by 1 h under vacuum. The mixture was dissolved in anh. CH$_2$Cl$_2$ and cooled to –78° C. for 15 min. Trimethylsilyltriflate (22 μL, 0.12 mmol) was added dropwise. After stirring for 10 min at –78° C., triethylamine (30 μL) was added. The solution was warmed to room temperature and the solvent was removed in a stream of N$_2$. The resulting crude product was purified by flash silica column chromatography to afford fully protected disaccharides and thioglycosides.

General Procedure E

α-Phosphate glycosyl donor (0.12 mmol) and glycosyl acceptor (0.10 mmol) were combined and azeotropically dried with toluene (3×5 mL) followed by 1 h under vacuum. The mixture was dissolved in anh. CH$_2$Cl$_2$ and cooled to –20° C. for 15 min. Trimethylsilyltriflate (22 μL, 0.13 mmol) was added dropwise. After stirring for 10 min at –20° C., triethylamine (30 μL) was added. The solution was warmed to room temperature and the solvent was removed in a seam of N$_2$. The resulting crude product was purified by flash silica column chromatography to afford fully protected disaccharides and thioglycosides.

Synthesis of 3,4,6-Tri-O-benzyl-2-O-pivaloyl-β-D-glucopyranoside-(1→6) 1,2:3,4-di-O-isopropylidene-α-D-galactopyranoside 13.

General Procedure D (94%). All spectral data matched that described in the scientific literature: Plante and Seeberger *J Org. Chem*.

Synthesis of Methyl 2-O-Pivaloyl-3,4,6-tri-O-benzyl-β-D-glucopyranoside-(1→2)-3,4,6-tri-O-benzyl-β-D-glucopyranoside 14.

General Procedure D (83%) [α]$^{24}_D$:–14.3° (c 1.65, CH$_2$Cl$_2$); IR (thin film) 2868, 1740, 1456, 1054 cm$^{-1}$; $^1$H-NMR (CDCl$_3$) δ7.42–7.26 (m, 28 H), 7.20–7.17 (m, 2H), 5.18 (t, J=8.50 Hz, 1H), 5.03 (d, J=8.00 Hz, 1H), 4.97 (d, J=11.5 Hz, 1H), 4.84–4.75 (m, 4H), 4.71–4.64 (m, 3H) 4.61–4.54 (m, 4H), 4.40 (d, J=14.0 Hz, 1H), 3.81–3.62 (m, 9H), 3.53 (s, 4H) 3.51–3.46 (m, 1H), 1.13 (s, 9H); $^{13}$C-NMR (CDCl$_3$) δ177.0, 139.0, 138.5, 138.3, 128.7, 128.6, 128.3, 128.1, 128.0, 127.8, 127.7, 127.5, 103.3, 99.8, 85.4, 84.0, 80.0, 78.2, 75.8, 75.3, 75.2, 75.0, 73.9, 73.8, 69.1, 69.0, 57.3, 39.1, 27.5; FAB MS m/z (M$^+$) calcd 980.4710, obsd 980.4708.

Synthesis of 3,4-Di-O-benzyl-2-O-pivaloyl-6-O-triisopropylsily-β-D-glucopyrano-side-(→6)1,2,3,4-di-O-isopropylidene-α-D-galactopyranoside 15

General Procedure D (82%) [α]$^{24}_D$: –37.7° (c 1.37, CH$_2$Cl$_2$); IR (thin film) 2964, 2868, 1740, 1650, 1037 cm$^{-1}$; $^1$H-NMR (CDCl$_3$) δ7.34–7.26 (m, 10H), 5.49 (d, J=5.00 Hz, 1H), 5.04 (t, J=8.75 Hz, 1H), 4.79 (t, J=9.00 Hz, 2H), 4.70 (t, J=9.00 Hz, 2H), 4.57 (d, J=8.00 Hz, 1H), 4.45 (d, J=8.00 Hz, 1H), 4.28–4.27 (m, 1H), 4.26 (t, J=15.0 Hz, 1H), 4.04–3.98 (m, 3H), 3.90 (t, J=5.75 Hz, 1H), 3.81 (t, J=9.25 Hz, 1H), 3.71 (t, J=9.25 Hz, 1H), 3.56 (dd, J=6.00 10.0 Hz, 1H), 3.34 (d, J=9.50 Hz, 1H), 1.50 (s, 3H), 1.44 (s, 3H), 1.33 (s, 3H), 1.31 (s, 3H), 1.20 (s, 9H), 1.14–1.09 (m, 21H); $^{13}$C-NMR (CDCl$_3$) δ177.1, 138.5, 128.6, 128.5, 128.1, 127.9, 127.8, 127.7, 109.2, 108.6, 101.4, 96.4, 83.5, 77.5, 76.4, 75.2, 75.1, 73.3, 71.2, 70.8, 70.7, 68.1, 67.1, 62.4, 39.0, 27.4, 26.3, 26.2, 25.2, 2 4.5, 18.2, 12.2; FAB MS m/z (M) calcd 842.4636, obsd 842.4639.

Synthesis of 3,4,6-Tri-O-benzyl-β-D-glucopyranoside-(1→6)-1,2:3,4-di-O-isopropylidene-α-D-galactopyranoside 16

General Procedure D (71%) [α]$^{24}_D$:–45° (c 0.61, CH$_2$Cl$_2$); IR (thin film) 3474, 2916, 1453, 1381, 1068 cm$^{-1}$; $^1$H-NMR (CDCl$_3$) δ7.42–7.25 (m, 13H),7.17–7.13 (m, 2H), 5.57 (d, J=5.29 Hz, 1H), 5.03 (d, J=11.2 Hz, 1H), 4.83 (t, J=10.9 Hz, 2H), 4.64–4.60 (m, 2H), 4,55–4.49 (m, 2H), 4.37–4.32 (m, 2H), 4.23 (dd, J=1.87, 7.79 Hz, 1H), 4.12 (dd, J=3,43, 10.9 Hz, 1H), 4.06–4.01 (m, 1H), 3.78–3.70 (m, 3H), 3.63–3.61 (m, 3H), 3.52–3.47 (m, 1H), 3.04 (bs, 1H), 1.55 (s, 3H), 1.46 (s, 3H), 1.35 (s, 3H), 1.33 (s, 3H); $^{13}$C-NMR (CDCl$_3$) δ138.9, 138.2, 128.5, 128.0, 127.8, 127.7, 109.7, 109.0, 104.2, 96.4, 84.8, 77.5, 75.3, 75.0, 73.7, 71.4, 70.9, 70.6, 69.7, 69.0, 68.1, 26.3, 26.2, 25.3, 24.7; FAB MS m/z (M$^+$) calcd 692.3196, obsd 692.3192.

Synthesis of Thioethyl 3,4,6-Tri-O-benzyl-2-O-pivaloyl-β-D-glucopyranoside 17

General Procedure D (90%) All spectral data matched that described in Seeberger et al. *J Am. Chem. Soc.* 1997, 119, 10064.

Synthesis of Thioethyl 2-O-pivaloyl-3,4,6-tri-O-benzyl-β-D-glucopyranoside-(1→6)-3,4-di-O-benzyl-2-O-pivaloyl-β-D-mannopyranoside 18

General Procedure D (83%) [α]$^{24}_D$:–38.30° (c 1.14, CH$_2$Cl$_2$); IR (thin film) 2968, 2869, 1734, 1453,1364 cm$^{-1}$; $^1$H-NMR (CDCl$_3$) δ7.35–7.24 (m, 23H), 7.18–7.16 (m, 2H),5.56 (d, J=2.50 Hz, 1H), 5.10 (t, J=8.50 Hz, 1H), 4.84 (d, J=11.0 Hz, 1H), 4.79–4.74 (m, 2H), 4.72–4.68 (m, 2H), 4.62–4.50 (m, 6H), 4.43 (d, J=11.0 Hz, 11), 4.06 (d, J=11.0 Hz, 1H), 3.75–3.66 (m, 5H), 3.61–3.56 (m, 3H), 3.41 (t, J=9.50 Hz, 1H), 2.73 (q, J=7.50 Hz, 2H), 1.30 (t, J=7.50 Hz, 3H), 1.26 (s, 9H), 1.20 (s, 9H); $^{13}$C-NMR (CDCl$_3$) δ177.9, 176.9, 138.4, 138.3, 138.1, 128.7, 128.6, 128.5, 128.4, 128.3, 128.2, 128.1, 128.0, 127.9, 127.8, 127.7, 101.4, 83.7, 82.4, 82.0, 79.8, 78.2, 75.4, 75.3, 75.1, 74.7, 73.9, 73.2, 71.8, 69.5, 69.4, 69.1, 39.4, 39.1, 27.6, 27.5, 25.9, 15.4; FAB MS m/z (M$^+$) calcd 1004.4744, obsd 1004.4741.

Synthesis of 2-O-pivaloyl-3,4,6-tri-O-benzyl-β-D-glucopyrano-side-(6)-3,4-di-O-benzyl-2-O-pivaloyl-α-D-mannopyranoside (1→4)-3,6-di-O-benzyl-D-arabino-hex-1-enitol 20

A mixture of thioethyl glycosyl donor 18 (55.3 mg, 0.055 mmol) and 3,6-di-O-benzylglucal 19 (16.3 mg, 0.050 mmol) was azeotroped with toluene (3×3 mL) and dried under vacuum for 1 h. CH$_2$Cl$_2$ (1 mL) was added to the mixture along with 60 mg freshly dried 4Å molecular sieves. The solution was cooled to 0° C. and di-tert-butylpyridine (45 μL, 0.20 mmol) was added. After stirring at 0° C. for 30 min, methyl triflate (22 μL, 0.20 mmol) was added. Stirring was continued for 16 h at 0° C. followed by gradual warning to room temperature over 1 h. Triethylamine (50 μL) was added and stirring continued for 30 min. The solvent was removed in a stream of $N_2$ and the residue purified by flash silica column chromatography to afford trisaccharide 20 (44 mg, 68% yield). $[\alpha]^{24}_D$:−6.1° (c 0.89, $CH_2Cl_2$); IR (thin film) 2967, 2870, 1734, 1649, 1454 cm$^{-1}$; $^1$H-NMR ($CDCl_3$) δ7.35–7.24 (m, 33H), 7.16–7.13 (m, 2H), 6.44 (d, J=6.50 Hz, 1H), 5.36–5.34 (m, 1H), 5.19 (d, J=1.50 Hz, 1H), 5.14 (t, J=8.25 Hz, 1H), 4.89–4.87 (m, 1H), 4.83 (d, J=11.0 Hz, 1H), 4.77 (d, J=11.5 Hz, 1H), 4.73–4.67 (m, 2H), 4.64–4.42 (m, 1H), 4.26–4.22 (m, 1H), 4.11–4.08 (m, 1H), 4.05–4.03 (m, 2H), 3.92–3.88 (m, 2H), 3.84–3.78 (m, 2H), 3.71–3.62 (m, 6H), 3.54–3.30 (m, 1H), 1.19 (s, 9H), 1.15 (s, 9H); $^{13}$C-NMR ($CDCl_3$) δ177.7, 176.6, 144.9, 138.6, 138,5, 138.4, 138.3, 138.2, 128.5, 128.4, 128.2, 128.1, 128.0, 127.9, 127.7, 127.6, 127.5, 101.2, 99.0, 97.8, 83.5, 78.3, 78.1, 76.5, 75.6, 75.1, 74.9, 74.6, 73.8, 73.7, 73.5, 72.9, 72.2, 71.8, 71.5, 70.0, 69.2, 69.0, 68.5, 68.0, 67.0, 39.1, 38.9, 27.4; FAB MS m/z (M$^+$) calcd 1268.6072, obsd 1268.6075.

Incorporation By Reference

All of the references and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of glycosylating a substrate, comprising the step of:

combining a compound represented by 1 with a substrate comprising an —OH, —NH—, or —SH moiety under reaction conditions whereby said moiety of said substrate reacts with 1 to produce a glycosylated substrate, wherein said reaction conditions comprise a Lewis acid selected from the group consisting of silyl sulfonates, silyl sulphates, silyl carboxylates, silyl phosphates, silyl halides, and boron trihalides; and wherein 1 is represented by the following structure:

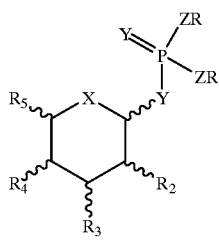

1 wherein

X represents O, NR', or S;

Y represents independently for each occurrence O, NR', or S;

Z represents independently for each occurrence O or S;

R is selected, independently for each occurrence, from the group consisting of H, alkyl, heteroalkyl, aryl, aralkyl, heteroaryl, and heteroaralkyl;

R' is selected, independently for each occurrence, from the group consisting of H, alkyl, heteroalkyl, aryl, aralkyl, heteroaryl, heteroaralkyl, acyl, and sulfonyl;

$R_2$, $R_3$, and $R_4$ are independently selected from the group consisting of R, —OR', —SR—, —NR'$_2$, —OSO$_3$H, —OPO$_3$H$_2$;

$R_5$ is selected from the group consisting of R, —(CR$_2$)$_n$OR', —(CR$_2$)$_n$SR', and —(CR$_2$)$_n$NR'$_2$; and n is an integer selected from the range 0 to 10 inclusive.

2. The method claim 1, further comprising the step of:

purifying said glycosylated substrate.

3. The method of claim 1 or 2, further comprising the step of:

combining said glycosylated substrate with 1 under reaction conditions whereby an —OH, —NH—, or —SH moiety of said glycosylated substrate reacts with 1 to produce a glycosylated substrate comprising at least two sugar moieties derived from compounds represented by 1.

4. The method of claim 3, wherein said reaction conditions comprise a silyl sulfonate.

5. The method of claim 3, wherein said reaction conditions comprise a silyl triflate.

6. The method of claim 3, wherein said reaction conditions comprise a trialkylsilyl triflate.

7. The method of claim 3, wherein said reaction conditions comprise trimethylsilyl triflate.

8. The method of claim 1 or 2, wherein said reaction conditions comprise a silyl sulfonate.

9. The method of claim 1 or 2, wherein said reaction conditions comprise a silyl triflate.

10. The method of claim 1 or 2, wherein said reaction conditions comprise a trialkylsilyl triflate.

11. The method of claim 1 or 2, wherein said reaction conditions comprise trimethylsilyl triflate.

12. The method of claim 1 or 2, wherein said glycosylated product is produced in greater than about 50% yield based on 1.

13. The method of claim 1 or 2, wherein said glycosylated product is produced in greater than about 70% yield based on 1.

14. The method of claim 1 or 2, wherein said glycosylated product is produced in greater than about 80% yield based on 1.

15. The method of claim 1 or 2, wherein said glycosylated product is produced in greater than about 90% yield based on 1.

16. A combinatorial method of synthesizing libraries of oligosaccharides, comprising the steps of: dividing a sample of substrate into a plurality of portions; reacting each portion of substrate with a single glycosyl donor; wherein not all portions of substrate are reacted with the same glycosyl donor, and the glycosyl donors are selected from the set consisting of glycals, glycosyl halides, compounds of claim 1, anhydrosugars, N-pentenyl glycosides, glycosyl sulfides, trichloroacetimidates, glycosyl sulfates, and glycosyl carboxylates; and purifying and combining the products of the previous step.

17. A method of synthesizing a compound represented by 1, wherein said method is represented by the following scheme:

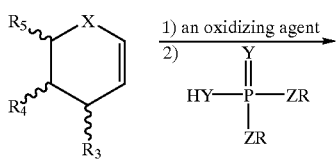

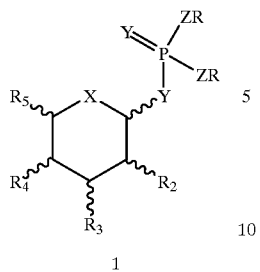

1 wherein

X represents O, NR', or S;

Y represents independently for each occurrence NR' or S;

Z represents independently for each occurrence O, NR', or S;

the oxidizing agent is selected from the group consisting of dioxiranes, percarboxylates, and persulfates;

R is selected, independently for each occurrence, from the group consisting of H, alkyl, heteroalkyl, aryl, aralkyl, heteroaryl, and heteroaralkyl;

R' is selected, independently for each occurrence, from the group consisting of H, alkyl, heteroalkyl, aryl, aralkyl, heteroaryl, heteroaralkyl, acyl, and sulfonyl;

$R_2$ is OR';

$R_3$, and $R_4$ are independently selected from the group consisting of R, —OR', —SR', —NR'$_2$, —OSO$_3$H$_2$;

$R_5$ is selected from the group consisting of R, —(CR$_2$)$_n$OR', —(CR$_2$)$_n$SR', and —(CR$_2$)$_n$NR'$_2$; and n is an integer selected from the range 0 to 10 inclusive.

18. The method of claim 17, wherein the oxidizing agent is a dioxirane.

19. The method of claim 18, wherein the oxidizing agent is dimethyl dioxirane (DMDO).

* * * * *